United States Patent [19]

Mechoulam et al.

[11] Patent Number: 5,521,215

[45] Date of Patent: *May 28, 1996

[54] NMDA-BLOCKING PHARMACEUTICALS

[75] Inventors: Raphael Mechoulam, Jerusalem; Mordechai Sokolovsky, Tel Aviv; Yoel Kloog, Hertzlyia; Anat Biegon, Tel Aviv, all of Israel

[73] Assignees: Ramot University Authority for Applied Research and Industrial Development Ltd., Tel Aviv; Yissum Research Development Company of the Hebrew University in Jerusalem, Jerusalem, both of Israel; Pharmos Corp., New York, N.Y.

[*] Notice: The term of this patent shall not extend beyond the expiration date of Pat. No. 5,284,867.

[21] Appl. No.: 192,886

[22] Filed: Feb. 7, 1994

Related U.S. Application Data

[63] Continuation-in-part of Ser. No. 865,088, Apr. 8, 1992, Pat. No. 5,284,867, which is a continuation of Ser. No. 609,588, Nov. 6, 1990, abandoned.

[30] Foreign Application Priority Data

Nov. 7, 1989 [IL] Israel ............................................ 92238

[51] Int. Cl.⁶ .................................................... A61K 31/35
[52] U.S. Cl. ........................................................ 514/454
[58] Field of Search ..................... 549/454, 390; 514/454

[56] References Cited

U.S. PATENT DOCUMENTS

| | | |
|---|---|---|
| 4,133,819 | 1/1979 | Johnson . |
| 4,179,517 | 12/1979 | Mechoulam et al. . |
| 4,209,520 | 6/1980 | Johnson . |
| 4,876,276 | 10/1989 | Mechoulam et al. . |

FOREIGN PATENT DOCUMENTS 28 26 849  12/1978  Germany .

OTHER PUBLICATIONS

Mechoulam et al., Tetrahedron Asymmetry 1:315–319 (1990).
Choi, Neuron 1:623–624 (1988).
Kloog et al., Biochemistry 27:843–848 (1988).
Mechoulam et al., Experientia 44:762–764 (1988).
Feigenbaum et al., Pharmacol. Biochem. Behav. 16:235–240 (1982).

*Primary Examiner*—Nicky Chan
*Attorney, Agent, or Firm*—Pennie & Edmonds

[57] ABSTRACT

Pharmaceutical compositions are described for preventing neurotoxicity, comprising as active ingredient the stereospecific (+) enantiomer, having (3S,4S) configuration of $\Delta^6$ tetrahydrocannabinol type compounds. The compositions are particularly effective in alleviating and even preventing neurotoxicity due to acute injuries to the central nervous system, including mechanical trauma, compromised or reduced blood supply as may occur in cardiac arrest or stroke, or poisonings. They are also effective in the treatment of certain chronic degenerative diseases characterized by gradual neuronal loss.

8 Claims, 10 Drawing Sheets

▨ mild

▨ moderate (a) HU-211 Vs. Untreated P<0.02
(b) HU-211 Vs. Vehicle P<0.05

▨ Untreated    ☐ HU-211
▨ Vehicle      ▥ Naive

NMDA-BLOCKING PHARMACEUTICALS

CROSS-REFERENCES TO RELATED APPLICATIONS

This is a continuation-in-part of application Ser. No. 07/865,088, filed Apr. 8, 1992, now U.S. Pat. No. 5,284,867, which in turn was a continuation of application Ser. No. 07/609,588, filed Nov. 6, 1990, now abandoned.

FIELD OF THE INVENTION

The present invention relates to pharmaceutical compositions for preventing or alleviating neurotoxicity. Said pharmaceutical compositions comprise as their active ingredient the stereospecific (+) enantiomers, having (3S,4S) configuration, of $\Delta^6$-tetrahydrocannabinol (THC) type compounds of general formula (I), as defined hereinbelow.

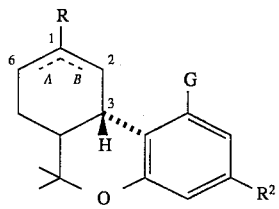

BACKGROUND OF THE INVENTION

Chronic degenerative changes, as well as delayed or secondary neuronal damage following direct injury to the central nervous system (CNS), may result from pathologic changes in the brain's endogenous neurochemical systems. Although the precise mechanisms mediating secondary damage are poorly understood, post-traumatic neurochemical changes may include overactivation of neurotransmitter release or re-uptake, changes in presynaptic or postsynaptic receptor binding, or the pathologic release or synthesis of endogenous factors. The identification and characterization of these factors and of the timing of the neurochemical cascade after CNS injury provides a window of opportunity for treatment with pharmacologic agents that modify synthesis, release, receptor binding, or physiologic activity with subsequent attenuation of neuronal damage and improvement in outcome. A number of studies have suggested that modification of post-injury events through pharmacologic intervention can promote functional recovery in both a variety of animal models and clinical CNS injury. Pharmacologic manipulation of endogenous systems by such diverse pharmacologic agents as anticholinergics, excitatory amino acid antagonists, endogenous opioid antagonists, catecholamines, serotonin antagonists, modulators of arachidonic acid, antioxidants and free radical scavengers, steroid and lipid peroxidation inhibitors, platelet activating factor antagonists, anion exchange inhibitors, magnesium, gangliosides, and calcium channel antagonists have all been suggested to potentially improve functional outcome after brain injury (Mcintosh, *J. Neurotrauma* 10: 215–243, 1993).

The pathogenesis of a diverse group of neurological disorders has been linked to excessive activation of excitatory amino acid receptors. These disorders include epilepsy, focal and global ischemia, CNS trauma, and various forms of neurodegeneration including Huntington's chorea, Parkinson's disease and Alzheimer's disease. There has been extensive effort invested in the development of excitatory amino acid receptor antagonists as therapeutic agents (Rogawski, M. A., Trends in *Pharmacol. Sci.* 14: 325–331, 1993).

Since no proven effective therapy for neuronal injury, or degeneration, is yet known, and, for example, stroke alone is one of the leading causes of death in many countries, the importance of finding such thereapeutic NMDA antagonists is self-evident. It will be important to determine whether certain NMDA antagonists are more effective—or have fewer side effects—than others in specific disease states.

Some of the compounds of general formula (I) are disclosed in U.S. Pat. Nos. 4,179,517 and 4,876,276. As disclosed in said U.S. patents, these essentially pure synthetic (+)-(3S,4S)-THC derivatives and analogues are devoid of any undesired cannabimimetic psychotropic side-effects. These known compounds have been described as having analgesic, antiemetic and antiglaucoma activity.

The inventors have now found that the said known compounds, as well as some novel compounds, in addition to having said analgesic, antiemetic and anti-glaucoma activity, are also effective against the diseases and conditions mentioned above, possibly as excitatory amino acid receptor blockers, for example NMDA- or glutamate-blockers or interaction with the glycine receptor, and are effective in the alleviation and treatment of many of the abnormal states involving said neurotransmitter mediated toxicity.

SUMMARY OF THE INVENTION

The compositions of the present invention are particularly effective in alleviating and even preventing glutamate neurotoxicity due to acute injuries to the central nervous system (CNS), such as injuries due to prolonged seizures, compromised or reduced blood supply, deprivation of glucose supply and mechanical trauma. The present compositions are also effective in alleviating other damages to the CNS like poison-induced convulsions, considered to be associated with amino acid receptors other than that of glutamate, for example glycine.

The compositions of the present invention may also be effective in the treatment of certain chronic degenerative diseases which are characterized by gradual selective neuronal loss. In this connection, the compositions of the present invention are contemplated as therapeutically effective in the treatment of Alzheimer's disease.

The present compositions are of special value in grand mal seizures, global hypoxic ischemic insults, in hypoxia, alone or in combination with blood flow reduction (ischemia), as well as in cases of cardiac arrest and in cases of abrupt occlusion of cerebral arteries (stroke).

Some of the compounds according to formula (I), as will be hereinafter described in detail, are novel compounds and are claimed as such within the scope of the present application.

DETAILED DESCRIPTION OF THE INVENTION

Figure 1:
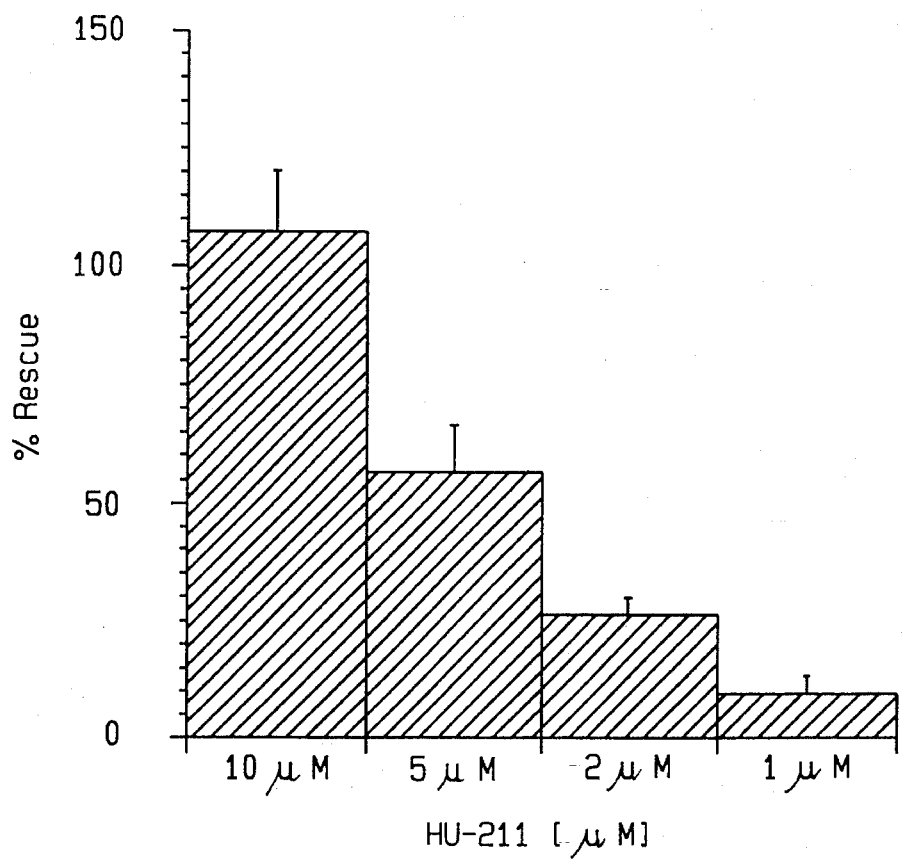
FIG. 1 shows concentration dependence of HU-211 blockade of NMDA-induced toxicity in cultured neurons

The present invention provides pharmaceutical compositions to reduce or even prevent excitatory amino acid neurotoxicity, due to acute injury or poisoning of the CNS, such as injuries due to prolonged seizures, compromised or reduced blood supply, deprivation of glucose supply and mechanical trauma, and poisonings by, for example, strychnine, picrotoxin or organophosphorous compounds.

The compositions of the present invention may also be effective in treating certain chronic degenerative diseases which are characterized by gradual selective neuronal loss. In this connection, the compositions of the present invention are contemplated as therapeutically effective in the treatment of Huntington's chorea, Parkinson's disease and Alzheimer's disease.

As stated above, the present compositions are of special value in seizures, global hypoxic ischemic insults, in hypoxia, alone or in combination with blood flow reduction (ischemia) as well as in cases of cardiac arrest and in cases of abrupt occlusion of cerebral arteries (stroke).

The present invention relates to pharmaceutical compositions for the purposes set out above, in which the active ingredient is a compound of the general formula:

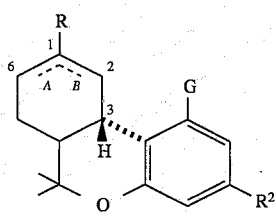

(I)

having the (3S,4S) configuration and being essentially free of the (3R,4R) enantiomer, wherein A-----B indicates an optional 1(2) or 6(1) double bond, R is (a) —Q wherein Q is a heterocyclic moiety having a labile hydrogen atom so that said moiety acts as a carboxylic acid analogue, (b) —R'X wherein R' is $C_1$–$C_5$ alkyl and X is halogen, —OR' wherein R' is $C_1$–$C_5$ alkyl, or —OC(O)R''' wherein R''' is hydrogen or $C_1$–$C_5$ alkyl, (c) —R'N(R'')$_2$ wherein R' is $C_1$–$C_5$ alkyl and each R'', which may be the same or different, is hydrogen or $C_1$–$C_5$ alkyl optionally containing a terminal —OR''' or —OC(O)R''' moiety wherein R''' is hydrogen or $C_1$–$C_5$ alkyl, (d) —R' wherein R' is $C_2$–$C_5$ alkyl, or, when A-----B is absent, (e) —R'OR''' wherein R' is $C_1$–$C_5$ alkyl and R''' is hydrogen or $C_1$–$C_5$ alkyl, G is (a) halogen, (b) $C_1$–$C_5$ alkyl, or (c) —OR$_1$ wherein R$_1$ is (a') —R'', wherein R'' is hydrogen or $C_1$–$C_5$ alkyl optionally containing a terminal —OR''' or —OC(O)R''' moiety wherein R''' is hydrogen or $C_1$–$C_5$ alkyl, or (b')—C(O)R''' wherein R''' is as previously defined, and R$_2$ is (a) $C_1$–$C_{12}$ alkyl, (b) —OR'''', in which R'''' is a straight chain or branched $C_2$–$C_9$ alkyl which may be substituted at the terminal carbon atom by a phenyl group, or (c) —(CH$_2$)$_n$OR''' wherein n is an integer of 1 to 7 and R''' is hydrogen or $C_1$–$C_5$ alkyl.

In a currently preferred group of compounds, $R^2$ designates a 1,1-dimethylalkyl radical or a 1,2-dimethylalkyl radical with a total of at least 7 carbon atoms. Also preferred are precursors of such compounds. Particularly preferred compounds are those wherein $R^2$ is 1,1-dimethylheptyl or 1,2-dimethylheptyl. It is these embodiments of $R^2$ that are found in THC and its analogues. However, for the neuroprotective activity that characterizes the present invention, it is believed that any lower or mid-range alkyl substituent will be suitable at this position.

A preferred compound, with which many of the physiological experiments have been carried out, is the compound which may be referred to as the (+)-(3S,4S)-1,1-dimethylheptyl homolog of 7-hydroxy-$\Delta^6$-tetrahydrocannabinol. Said compound is designated hereinafter as HU-211.

It is stressed that all the compounds are of the (+)-(3S,4S) configuration, essentially free of the (−)-(3R,4R) enantiomer, the latter known to possess the undesired psychotropic side-effects. Thus, for example, the enantiomers of the synthetic cannabinoid 7-hydroxy-$\Delta^6$-tetrahydrocannabinol 1,1-dimethylheptyl homolog, have been described [Mechoulam, R., et al., Tetrahedron:Asymmetry 1: 315–319, 1990; Mechoulam, R. et al., Experientia 44: 762–764, 1988]. The (−)-(3R,4R) enantiomer, herein designated HU-210, is a highly potent cannabimimetic compound (nearly 100 times more active than Δ-1-tetrahydrocannabinol, the active component of hashish). The (+)-(3S,4S) enantiomer, herein designated HU-211, while known to be active as an analgesic and as an anti-emetic, is inactive as a cannabimimetic even at doses several thousand times higher than the ED$_{50}$ of HU-210 (Mechoulam, R. et al., Experientia 44: 762–764, 1988). As mentioned above, then, the compounds of the general formula (I) as defined herein are substantially devoid of cannabimimetic central nervous system activity.

| TABLE OF ABBREVIATIONS USED THROUGHOUT THE TEXT | |
| --- | --- |
| AMPA | α-amino-3-hydroxy-5-methylisoxazole-4-propionic acid (an excitatory amino acid which identifies a subset of receptors) |
| ANOVA | analysis of variance |
| BBB | blood brain barrier |
| CAPS | compound action potentials |
| CBF | cerebral blood flow |
| CCA | common carotid artery |
| CNS | central nervous system |
| FAM | mixture of 40% formaldehyde:acetic acid:methanol, 1:1:8 by volume |
| FUDR | fluorouridine |
| HPCD | hydroxypropyl-β-cyclodextrin |
| HT | head trauma |
| IR | infrared |
| MAP | mean arterial blood pressure |
| MCA | middle cerebral artery |

TABLE OF ABBREVIATIONS USED THROUGHOUT THE TEXT

| | |
|---|---|
| MCAo | middle cerebral artery occlusion |
| MEM | minimal essential medium |
| MK-801 | Merck compound 801, i.e. 10,11-dihydro-5-methyl-5H-dibenzo[a,d]cyclohepten-5,10-imine |
| [$^3$H]MK-801 | tritiated MK-801 |
| MRI | magnetic resonance imaging |
| NADH | nicotinamide adenine dinucleotide |
| NMDA | N-methyl-D-aspartic acid (an excitatory amino acid which identifies a subset of receptors) |
| NMR | nuclear magnetic resonance |
| NSS | neurological severity score |
| SG | specific gravity |
| SNP | sodium nitroprusside |
| TEA | triethylammonium |
| THC | tetrahydrocannibinol |
| UV | ultraviolet |
| VEP | visual evoked potential |
| XTT | 2,3-bis(2-methoxy-4-nitro-5-sulfophenyl)-2H-tetrazolium-5-carboxanilide |

Pharmacology

The novel compositions contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration or for injection, the term including subcutaneous, transdermal, intravenous, intrathecal, and other parenteral routes of administration. The liquid compositions include aqueous solutions, with or without organic cosolvents, aqueous or oil suspensions, flavored emulsions with edible oils, as well as elixirs and similar pharmaceutical vehicles. In addition, the compositions of the present invention may be formed as aerosols, for intranasal and like administration.

The active dose for humans is generally in the range of from 0.05 mg to about 50 mg per kg body weight, in a regimen of 1–4 times a day. However, administration every two days may also be possible, as the drug has a rather prolonged action. The preferred range of dosage is from 0.1 mg to about 20 mg per kg body weight. However, it is evident to the man skilled in the art that dosages would be determined by the attending physician, according to the disease to be treated, method of administration, patient's age, weight, contraindications and the like.

All the compounds defined above are effective NMDA-receptor blockers and can be used as active ingredients of pharmaceutical compositions for treatment of one, or simultaneously several, symptoms of the disorders defined above. The effective dosages are essentially similar, and the more pronounced effect is that of NMDA-receptor blocking, in addition to the known characteristics of these compounds. However, it is important to note that the compounds and compositions of the present invention exhibit good blocking activity also against convulsants which may not necessarily be NMDA-receptor mediators. For example, the compositions of the present invention can prevent, or at least alleviate, poisoning caused by strychnine organophosphorous compounds and nitrous oxide.

The compounds of the present invention are administered for the above defined purposes in conventional pharmaceutical forms, with the required solvents, diluents, excipients, etc. to produce a physiologically acceptable formulation. They can be administered by any of the conventional routes of administration. The required dose for humans ranges from 0.005 mg/kg to about 50 mg/kg per unit dosage form. The most preferred dose range is from about 0.1 mg/kg to about 20 mg/kg body weight.

It will be appreciated that the most appropriate administration of the pharmaceutical compositions of the present invention will depend on the type of injury or disease being treated. Thus, the treatment of acute head trauma, stroke or ischemic brain damage resulting from cardiac arrest will necessitate systemic administration of the drug as rapidly as possible after induction of the injury. On the other hand, diminution or prophylaxis of chronic degenerative damage will necessitate a sustained dosage regimen.

HU-211 conveys significant neuroprotection in different models of head trauma, global brain ischemia and crushed optic nerve. This suggests neuroprotective potential in a wide spectrum of CNS diseases, poisonings or injuries, as detailed above, including conditions involving axonal damage such as that sustained in spinal cord injury. HU-211 is also particularly useful in treating neural edema, associated with trauma, infection, tumors or surgical procedures including craniotomies and spinal cord manipulation.

Moreover, the combined neuroprotective properties of HU-211, as well as the known anti-glaucoma properties of this class of compounds, leads to special consideration of retinal eye diseases, especially those which are associated with ischemic damage or a hostile biochemical environment.

The following are some major ocular disease groups that should be considered candidates for HU-211 therapy:

(1) Diabetic retinopathy which stems mainly from altered retinal capillary circulation that renders the retina ischemic.

(2) Age-related Macular Degeneration which is associated with slow deterioration of the retinal pigment epithelium that eventually leads to retinal cell death and tissue alterations.

(3) Retinal vascular occlusions that are relatively common and may cause considerable ischemic damage. All retinal occlusions, venous and arterial, including the optic nerve (ischemic optic neuropathy), as well as retinopathy of prematurity (oxygen toxicity in premature babies), may be included in this category.

(4) Any insult that may lead to secondary neural damage following direct retinal cell death, e.g. trauma, including surgical trauma such as laser burn injuries, inflammations, infections and degenerative processes.

(5) Chronic ischemic damage, including glaucomatous optic nerve damage.

(6) Toxic damage (e.g., chloroquine toxicity) and chronic malnutrition.

The invention also relates to methods of treatment of the various pathological conditions described above, by administering to a patient a therapeutically effective amount of the compositions of the present invention. The term administration as used herein encompasses oral, parenteral, intravenous, intramuscular, subcutaneous, transdermal, intrathecal, rectal and intranasal administration.

The inventors have discovered that HU-211 and the compounds of formulae (II and IIa), as well as the said novel monoesters which are preferred active agents of the presently claimed compositions, at doses in excess of 25 mg/kg body weight, induce stereotypy, locomotor hyperactivity and tachycardia effects typically caused by NMDA-receptor antagonists. At considerably lower doses of about 2.5 mg/kg body weight, they are potent blockers of NMDA-induced tremor, seizure and lethality (Feigenbaum et al., *Proc. Natl. Acad. Sci. U.S.*, 86: 9584–9587, 1989). Thus, a good separation has been achieved between the therapeutic effects (NMDA antagonism) and possible side effects (such as tachycardia). Binding studies show that HU-211 blocks NMDA receptors in a stereospecific manner, and that the interaction occurs at binding site(s) distinct from those of some other non-competitive NMDA antagonists or of glutamate and glycine. This, and the other compounds according to formula (I), may therefore prove useful as non-psychoactive drugs that protect against NMDA-receptor-mediated neurotoxicity.

It was shown previously that the pharmacological profile of HU-211, and some other compounds constituting the active ingredients of the present compositions, includes the induction of stereotypy, locomotor hyperactivity and tachycardia in mice (Feigenbaum et al., 1989 ibid.). These properties are consistent with those of non-competitive antagonists of the NMDA sub-class of glutamate receptors, and suggest that these compounds are active NMDA-receptor antagonists. This possibility was explored by examining the activity of the compounds in protecting against the tremorogenic, convulsive and lethal effects of NMDA and NMDA agonists in mice. Such effects are counteracted by virtually all NMDA antagonists and, as expected, NMDA neurotoxicity was indeed blocked by HU-211 (Feigenbaum et al., 1989, ibid.).

Test systems

Evaluation of the therapeutic effects of HU-211 and its analogs has now been carried out in a series of experimental systems of increasing sophistication to support the utility of these drugs as neuroprotectants. The neuroprotective effects have been evaluated both in vitro and in vivo. These neuroprotective effects have been corroborated in the following systems:

(a) Binding to the MMDA receptor linked channel: Non competitive antagonists of NMDA, the primary example of which is the compound MK-801, bind to a site within the NMDA receptor channel thus preventing the activation of the receptor-channel complex and the consequent neurotoxicity. The ability of various compounds to compete with the binding of tritium labeled MK-801 to brain membranes is considered a measure of their potency as NMDA non-competitive antagonists.

(b) Blockage of MMDA toxicity in tissue culture: Neurons can be grown in culture and survive for several weeks. Application of NMDA to neuronal cultures results in toxicity to the neurons: microscopic viewing of the cultures shows reduced cell density and changes in the shape and staining properties of surviving neurons, and the metabolic activity in the cultures is greatly reduced, as assessed by reduction in the formation of a colored product from chemicals sensitive to the mitochondrial metabolic enzymes. The ability of various compounds to prevent the morphological and metabolic changes induced by NMDA is considered a measure of their neuroprotective activity in culture.

(c) Protection against hypobaric anoxia in mice: Exposure of mice to a hypobaric (200 mmHg) atmosphere reduces the amount of oxygen available to the animals and results in death within 1–2 minutes in untreated mice. Pretreatment with compounds that can counteract the effects of oxygen deprivation prolong (double or more) the survival time of mice subjected to this treatment. The increase in survival time is a measure of the potency of the compounds in counteracting anoxic damage in vivo.

(d) Improved clinical outcome after closed head injury in rats: Severe head injury is associated with high mortality and severe neurological impairment. Animals subjected to head trauma in a controlled fashion serve as models in which to test drugs of therapeutic potential. Test compounds can be evaluated both for improved clinical outcome and for reduction of edema induced by closed head injury. The ability of compounds to reduce the severity of neurological symptoms and to reduce brain edema is considered a measure of their potency in reducing brain damage.

(e) Inhibition of ischemic neuronal damage in gerbils: Temporary blockage of the blood supply to the gerbil brain by surgical ligation of the two major arteries (common carotids) results in transient global forebrain ischemia. Temporary global ischemia produces a delayed, selective degeneration of neurons in the hippocampus, a brain structure essential for memory formation. The ability of various compounds to prevent hippocampal cell loss and the attendant memory deficits is considered a measure of their potency as neuroprotectants in ischemic conditions.

(f) Optic nerve crush: Application of mechanical pressure to the optical nerve results in crush injury of the axons, which is accompanied by immediate changes in oxidative metabolism and delayed axonal death, which in turn is expressed in reduction of the compound action potential measurable from the nerve and loss of response to visual stimuli (blindness). The ability of various compounds to prevent the loss in metabolic activity, compound action potential and visually evoked potential is considered a measure of their potency in preventing the results of traumatic injury to axons.

(g) Middle cerebral artery occlusion (MCAO): The middle cerebral artery is the cerebral blood vessel most susceptible to stroke in humans. In animals, coagulation, permanent ligation or permanent placement of an occluding thread in the artery produces a permanent focal stroke affecting the MCA territory. Transient ligation or occlusion results in transient focal stroke. Both transient and permanent focal strokes result in varying degrees of edema and infarction in the affected brain regions. The ability of compounds to reduce the volumes of edema and infarction is considered a measure of their potential as anti-stroke treatment.

(h) Four vessel occlusion (4 VO) in rats: The blood supply to the rat brain arrives via the two vertebral and two common carotid arteries. Transient occlusion of all four vessels results in global ischemia, as would occur during cardiac arrest in humans. Global ischemia results in neurological deficits, including short term memory deficits, and a selective loss of neurons in the CA1 field of the hippocampus. The ability of compounds to reduce the neurological deficits and increase neuronal survival in this model is considered indicative of their potential in preventing brain damage related to cardiac arrest.

Each of these systems represents an aspect of neurotoxicity which is amenable to intervention by pharmaceutical agents that bind to the NMDA receptor. It is likely that the compounds of the present invention exert their demonstrated neuroprotective effects by virtue of their ability to bind to the NMDA receptor. Nevertheless, it cannot be ruled out that their activity is mediated by other receptors or additional mechanisms.

The prototype drug used for evaluation of NMDA blocking activity is the compound MK-801, which is a potent and selective NMDA antagonist that cannot be used as a human therapeutic agent due to its toxicity. We have evaluated the similarities and differences between the biological activities of MK-801 and HU211, as summarized in Table 1.

This evaluation clearly supports the concept that HU-211 is not acting solely as an NMDA antagonist. Rather the therapeutic effects of HU-211 may be attributable to additional mechanisms including antioxidant and radical scavenger properties, anticholinergic action, platelet activating factor antagonism, modulation of arachidonic acid, or inhibition of lipid peroxidation, among others. All of these types of pharmacologic agents have been suggested to potentially improve functional outcome after brain injury. All of these mechanisms may be involved in delayed, secondary or chronic neuronal damage following injury to the CNS (Mcintosh, *J. Neurotrauma* 20: 215–243, 1993).

TABLE 1

Properties of HU-211 and MK-801: Similarities and differences

| Assay (biological activity) | HU-211 | MK-801 |
| --- | --- | --- |
| oil/water partition | very lipophilic | water soluble |
| Binding to NMDA receptor channel | yes (low affinity) | yes (high affinity) |
| Binding to muscarinic receptors | yes | no |
| Binding to kainate/AMPA receptors | no | no |
| Blockade of NMDA toxicity in culture | yes | yes |
| Blockade of quisqualate toxicity in culture | partial | no |
| Blockade of NMDA induced Ca uptake | yes | yes |
| Blockade of NO (SNP*) toxicity | yes | no |
| Analgesia in mice | yes | no |
| Blockade of emesis in pigeons | yes | (not tested) |
| Behavioral toxicity in mice | low (high doses only) | high |
| Protection against global ischemia in gerbils (CCAo) | yes | yes |
| Protection against global ischemia in rats (4VO) | yes | no |
| Protection against closed head injury in rats | yes | poor (toxic) |

*SNP = sodium nitroprusside, a generator of nitrous oxide (NO).

Compounds

Experiments have shown that the (+)-(3S,4S) the compound of formula I wherein A-----B designates a 6(1) double bond, R is methyl, $R^1$ is hydrogen, and $R^2$ is 1,1-dimethylheptyl and the compound of formulas I wherein A-----B designates a 1(2) double bond, R is methyl, $R^1$ is hydrogen, and $R^2$ is 1,1-dimethylheptyl, both said compounds being essentially free of the (−)-(3R,4R) enantiomer, have practically the same activity as that of the compound designated HU-211. The former compound is designated compound Vb in U.S. Pat. No. 4,179,517; the latter compound is compound XIb therein.

In addition it has been found that some novel compounds of general formula (I), wherein R designates $CH_2R'$ and R' designates an acyl group also have the desired antiglutamate or glycine-associated activity. These novel compounds may be prepared, for example, by esterification of compounds of general formula (I) wherein R designates $CH_2OH$ and $R^1$ is hydrogen, under conditions which favor the formation of the desired monoesters with relatively high yield. Conventional esterification, for example, acetylation of the starting compound, which has two hydroxy moieties, using acetic anhydride and pyridine yields the diacetate, the monoacetate yield not exceeding 2–3%, which is of no practical synthetic value. The inventors had previously found that by conducting the esterification with an acid anhydride in the presence of potassium 2-methyl-2-butoxide, under nitrogen atmosphere, esterification on the phenyl ring hydroxy group is preferred and the desired monoester is obtained in high yield (U.S. patent application Ser. No. 07/865,088). The inventors have now found that, surprisingly, selective succinylation can be accomplished in the presence of triethylamine in boiling toluene, to yield the hemisuccinate substituted at the alkyl hydroxyl group of HU-211.

Among the novel compounds tested, monoesters including nicotinate, succinate and maleate are preferred. These novel compounds have the added advantage of being soluble in some aqueous solutions, whereas the parent compounds are extremely hydrophobic.

The following examples are intended to illustrate the present invention and these are to be construed in a non-limitative manner.

SYNTHETIC EXAMPLE 1

Esterification of HU-211 Synthesis of HU-211 hemisuccinate triethylammonium salt. 1.95 g HU-211 (0.005 mol) was dissolved in 50 ml of dry toluene and 0.51 g succinic anhydride (0.005 mol), dissolved in 50 ml toluene, was added to HU-211 solution. Mixture was placed into round-bottom flask, equipped with condenser, and refluxed 6 h. 700 mcl (0.5 g, 0.005 mol) of triethylamine was added, and mixture was refluxed overnight. Reaction was monitored by thin layer chromatography (TLC) on fluorescent labeled silica-gel plates, mobile phase—toluene:acetone 1:3. After complete elimination of HU-211 ($R_f$=0.86) in the reaction mixture organic solvent was completely evaporated with the aid of a rotatory evaporator (50 mmHg, 60° C). Residue was dissolved in 20 ml of diethyl ether and 20 ml n-heptane, and evaporated to dryness again, this stage was repeated twice for complete evacuation of toluene. TEA salt of HU-211 hemisuccinate was obtained as slightly yellowish viscous oil, yield is about 98%.

HU-211 hemisuccinate free acid. TEA salt of HU-211 hemisuccinate was dissolved in 100 ml 2% water solution of tris-(hydroxymethyl)aminomethane with the help of sonication (30 minutes) or wrist-shaker (2 hours), and poured into 500 ml cold solution of 2% HCl in water with intensive stirring. Sedimented HU-211 hemisuccinate free acid was collected, rinsed 3–5 times with pure water until the pH value of the wash rose to pH 4–5. The viscous product (water content about 60%) was collected and dissolved in 300 ml of diethyl ether. The solution was then dried for 24 h using large quantities of anhydrous $Na_2SO_4$ or $MgSO_4$, protected from light. After evaporation of the organic solvent in a rotary evaporator, a yellowish-orange, dry HU-211 hemisuccinate-free acid was obtained (yield about 65%). It is hygroscopic and must be stored refrigerated in a tightly closed vial.

Appearance. HU-211 hemisuccinate is an orange-yellow solid material, which is soluble in methanol, acetonitrile, and partially soluble in water.

Melting point. An average (n=5) melting point range of 50.3° –62.7° C. was observed for HU-211 hemisuccinate using a Haake Buchler melting point apparatus (S/N 17681B-77).

Infrared spectrum. An infrared spectrum of HU-211 hemisuccinate (prepared as a KBr pellet) was obtained on a Perkin Elmer Model 1600 FTIR (SN 134707). The infrared spectrum is consistent with the assigned structure.

Interpretation of the FT-IR spectrum of HU-211 hemisuccinate: IR(KBr,v,cm-1): 3424 and 3226(2x v OH), 2961(Vas CH$_3$), 2826(vas CH$_2$), 2894(vs CH$_3$), 2868(vs CH$_2$), 1736(vs C=O),1719(vs C=O),1625(v C=C, olefin), 1578(phenyl nucleus), 1459($\delta$CH$_3$), 1415,1384 and 1371(gem. dimethyl), 1267(vas C—O—C), 1186(vs C-O-C), 1085(v C-O phenol), 968($\gamma$CH, Ar), 839($\gamma$CH, olefin).

Ultraviolet spectrum. The UV spectrum of HU-211 hemisuccinate was recorded (as a 2.58×10$^{-4}$M solution in methanol) on a Shimadzu UV-160 spectrophotometer (S/N 1235621). The UV spectrum of the HU-2311 hemisuccinate sample prepared in methanol is consistent with the assigned structure (log $\epsilon_{276.0}$ =3.09 and log $\epsilon_{282.0}$=3.10).

Nuclear magnetic resonance spectra. Proton spectrum: the $^1$H-NMR spectrum of HU-211 hemisuccinate was recorded in methanol-d$_4$ on a Varian VXR 300 spectrometer. The $^1$H-NMR spectrum of HU-211 hemisuccinate is consistent with the proposed structure. $^{13}$C spectrum: The $^{13}$C-NMR spectrum of HU-211 hemisuccinate was recorded in methanol-d$_4$ on a Varian VXR 300 spectrometer. The $^{13}$C-NMR spectrum of HU-211 hemisuccinate is consistent with the proposed structure.

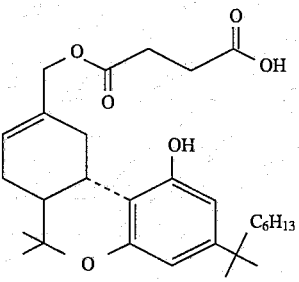

HU-211 Hemisuccinate
(6aS-trans)-6,6-dimethyl-3-(1,1-dimethylheptyl)-1-hydroxy-6a, 7,10,10a-tetrahydro-6H-dibenzo[b,d]pyran-9-methyl hemisuccinate C.    C28H42O66 MW 7-474.64

PHYSIOLOGICAL EXAMPLE 1

Neuroprotectant activity against toxicity mediated via glutamate receptors in cortical cultures.

The neuroprotective effects of the compounds of the invention were tested on neurons exposed to various excitotoxins in culture. The compounds tested included HU-211 and HU-211 acetate, which were previously shown to have NMDA antagonist properties in mice (U.S. patent application Ser. No. 07/865088 and HU-211 succinate).

Quantitative neurotoxicity studies. The test drugs were examined for their ability to protect neurons in culture from toxic effects of agonists of the different glutamate receptor subtypes (agonists of ionotropic and/or metabotropic glutamate receptors), e.g. NMDA, AMPA, kainate and quisqualate. The culture conditions and assay conditions were all performed as described in Eshhar et al., NeuroReport 5, 237–240 (1993). In brief, primary cerebral cortical cell cultures were prepared from 18–20 day old rat fetuses by enzymatic dissociation. Resulting cell suspensions were plated on confluent cortical glial cell feeder layer (prepared 2 weeks earlier by a similar method). Neurons were grown in MEM media containing 0.6% glucose, FUDR/Uridine mixture and N$_2$ supplement (insulin, progesterone, putrescine, selenium and transferrin). Cells at 10 days in culture were exposed to the various toxins either alone, or in the presence of the tested compounds. All exposures were carried out at 37° C. for 20–24 hours before assessing neuronal cell damage and neuroprotectant activity. Cell viability was determined morphologically following neuron specific enolase immunostaining of cells using the ABC biotin-avidin complex method, and determined quantitatively by measuring the extent of mitochondrial activity in living cells using the XTT-based assay. XTT (2,3-bis[2-methoxy-4-nitro-5 sulfophenyl]-2H-tetrazolium 5-carboxanilelide salt) is reduced by mitochondrial dehydrogenase to a soluble colored formazan. The density of color formation (O.D.), which is proportional to mitochondrial activity, was measured by a plate ELISA reader. The extent of neuroprotectant activity is expressed as % of cells rescued by the drugs tested.

Forebrain membrane preparation: Brains were removed from Sprague-Dawley rats no more than 5 min after decapitation. Membrane preparations were isolated according to a procedure described previously (Eshhar et al., Brain Res. 476:57, 1989). Prior to radioligand binding measurements, endogenous glutamate present in membranes was removed from the preparation by subjecting the membranes to 3–4 successive washings in 10 mM Tris HCl pH 7.2, performed at 4° C.

Radioligand binding studies: Binding of [$^3$H]MK-801 to membranes was conducted in the presence of 30 μM glycine and 10 μM L-glutamate. Membranes (250 μg protein) were resuspended in 50 mM tris-acetate pH 7.4 buffer and incubated with 10 nM [$^3$H]MK-801, either alone or in the presence of HU-211 at 0.195–100 μM concentrations for three hours at room temperature (RT). Reaction buffers used in the different radioligand binding studies contained 10% of an ethanol/Emulphor 620/deionized water mixture. The ratio (by volume) of the respective components in the mixture was 20/3/57. This mixture is required for solubilizing HU-211 at concentrations above 30 μM. Reaction volume was 1 ml. Non-specific [$^3$H]MK-801 binding was determined in the presence of 100 μM unlabeled MK-801. Binding of [$^3$H]AMPA of and [$^3$H]vinylidene-kainic acid to membranes was performed as described in Eshhar et al., 1993 (ibid.).

HU-211 neuroprotective activity: Co-application of 1000 μM NMDA and 10 μM HU-211 to cell cultures resulted in complete salvage of neurons from NMDA-induced toxicity. The morphological features of HU211 treated cells appeared similar to that of untreated sister cultures. HU-211 prevented both the neuronal cell body swelling and dendritic and axonal process degeneration produced by the toxin. The neuroprotectant activity of 10 μM HU-211 against NMDA-induced toxicity was comparable to that elicited by 30 μM MK-801. Enzyme-linked immunestaining with antibodies to enolase revealed dense staining in neuron cell bodies and processes of MK-801 and HU-211 treated cells. Staining intensity was similar to that produced by control cells of sister cultures. These morphological observations were confirmed by measuring mitochondrial activity in cells following injury and/or protection, using the XTT-based assay. The dose-response relationship of HU-211 required to protect against NMDA and quisqualate neurotoxicity was examined. NMDA-elicited neurotoxic effects were attenuated by HU-211 in a concentration-dependent manner. Half-maximal neuroprotection against NMDA mediated toxicity (EC$_{50}$) was observed at 3.8±0.9 μM HU211 (mean ±s.d.; n=3; FIG. 1). Neurotoxicity produced by exposing cells to 1000 quisqualate was attenuated by HU-211, although to a much lesser degree. The percent of cells rescued by 10 μM HU-211 was found to be 28.2±8%. By contrast, HU-211 failed to protect neurons from damage caused by the non-NMDA agonists—kainate or AMPA.

Figure 2:
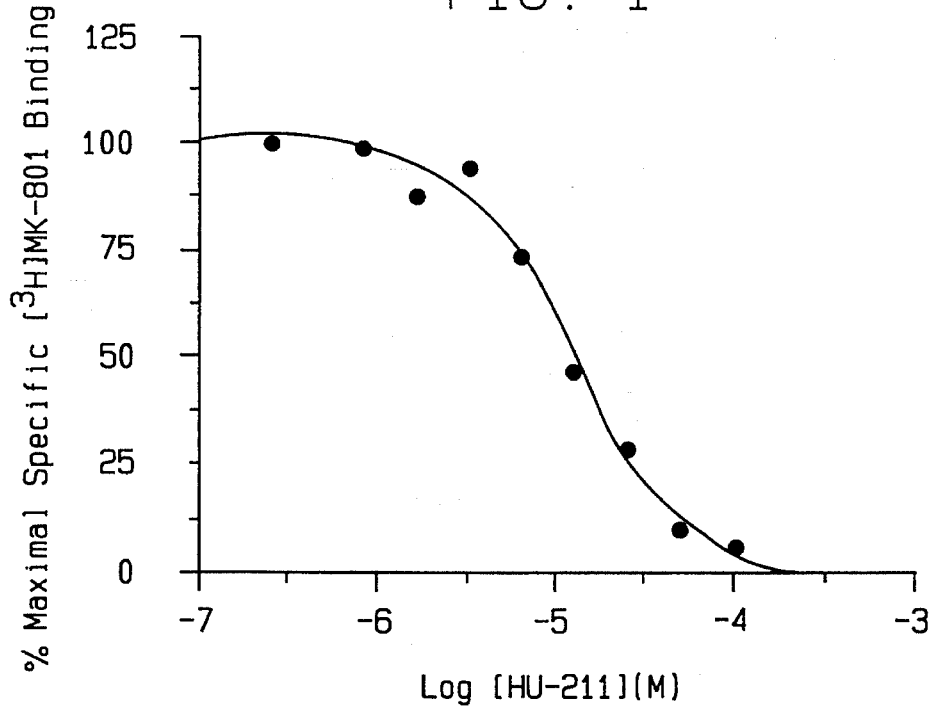
FIG. 2 shows inhibition of [3H]MK-801 binding to rat forebrain membranes by HU-211.

HU-211 mechanism of action as analyzed by radioligand binding studies: The identification of possible recognition sites for HU-211 at different glutamate receptor subtypes was carried out by measuring the ability of HU-211 to inhibit the binding of either MK-801, kainic acid or AMPA to rat forebrain membranes. Radioligand binding studies demonstrated that HU-211 competes with the binding of MK-801 to membranes, while it is unable to inhibit AMPA or kainic acid binding. Concentration dependence of HU-211 inhibition of [$^3$H]MK-801 binding is illustrated in FIG. 2. The inhibition constant ($K_i$) value displayed by HU-211 was measured and found to be 11.0±1.3 µM As deduced from Scatchard analyses, HU-211 greatly affected the affinity of [$^3$H]MK-801 to rat forebrain membranes. Significant decreases in affinity (increased $K_D$ values) were observed. The $K_D$ for [$_3$H]MK-801 binding was 40.5±2.5 nM, and 74.7±2.2 nM when HU-211 was added to the system. The apparent calculated $BM_{MAX}$ values for [$^3$H]MK-801 were 0.290±0.012 and 0.273±0.007 pmole/mg protein respectively. The respective $n_H$ values were found to be: 1.011±0.027 and 1.008±0.009. These data suggest that HU-211 displaces MK-801 binding in a competitive manner.

PHYSIOLOGICAL EXAMPLE 2

Neurotoxic effects of sodium nitroprusside in rat cortical cultures are attenuated by HU-211

The ability of HU-211 to prevent neuronal cell death induced by the nitric oxide (NO) donor sodium nitroprusside (SNP) was studied in rat cortical cell cultures. Neurotoxic effects of SNP can be attributed to NO which is spontaneously released by the compound or possibly to released cyanide. NO is an active agent in neurotoxicity and is an important neurotransmitter in the central and peripheral nervous system (Garthwaite, TINS 14: 60–67, 1991). It has been hypothesized that NO may be a mediator of neuronal damage during ischemia (Nowicki et al., J. Pharmacol., 204: 339, 1991) and it has been proposed as the chemical mediator that couples excitatory neurotransmission to excitotoxic cell death (Dawson et al., PNAS 88: 6368, 1991). Several lines of evidence have suggested that toxic actions of SNP might not result solely from the release of NO. As shown by Izumi et al. (Exp. Neurol. 121: 14, 1993), SNP neurotoxicity produced in rat hippocampal slices was not attenuated by MK-801. Moreover, that study suggested that SNP induces cell damage that differs from that produced by NMDA or cyanide.

METHODS

Preparation of cortical cell cultures: Cultures were prepared according to the procedure described above in example 1.

Exposure of cells to SNP and toxicity assessments: Cells at 10–14 days in culture were exposed to 0.5–10 mM SNP, either alone or in concert with 10 µM HU-211 (HPCD preparation) or 30 µM MK-801. All exposures were carried out for 20–24 hours at 37° C. before assessing neuronal cell death. Cells of sister cultures were exposed in parallel to vehicle only and were referred to as controls. Cell death was analyzed morphologically following immunocytochemical localization of neuron-specific enolase and assessed quantitatively using the XTT-based assay, as described in Physiological Example 1.

RESULTS

Figure 3:
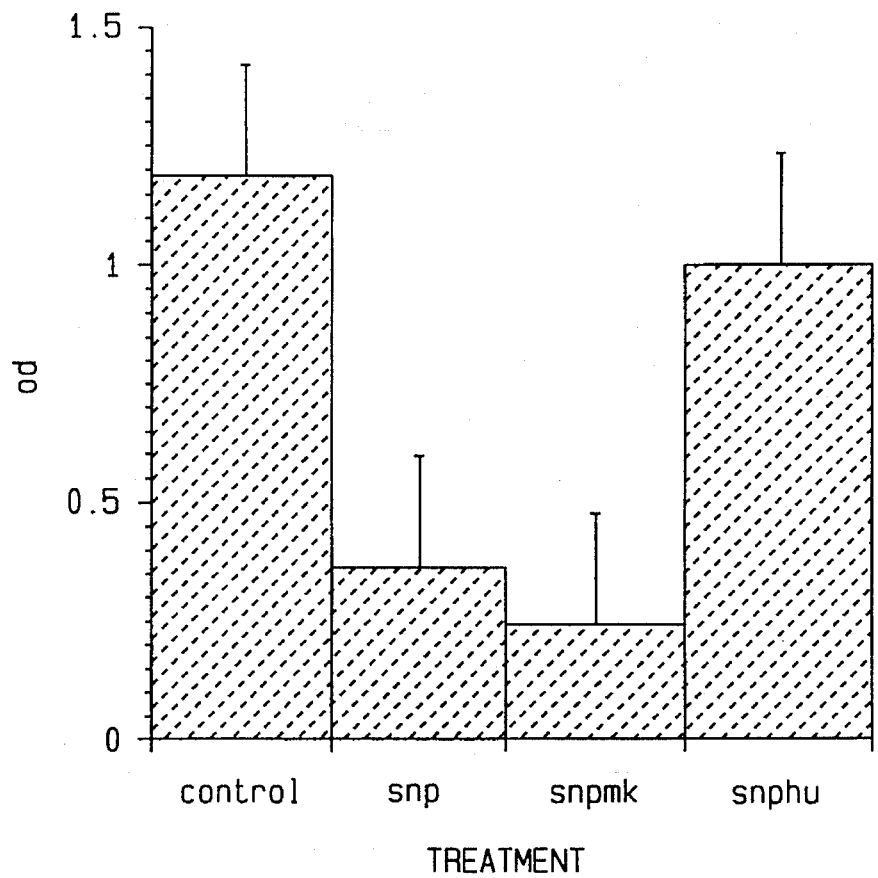
FIG. 3 shows rescue of neurons in culture from injury caused by sodium nitroprusside.

Incubation of cells with SNP produced a massive neuronal and glial cell damage. A dramatic attenuation in cell death was observed when cells were coincubated with HU-211 and SNP concentrations up to 5 mM. HU-211 was not effective when co-administered to cells with SNP at 10 mM concentration. Quantitative assessments of mitochondrial activity in cells have shown that HU-211 was able to rescue 75% of the cells from injury caused by 500 µM SNP (FIG. 3). No cell rescue was observed and measured when cells were coincubated with MK-801. Results are mean±S.E.M. of 3 experiments performed in sextuplicate.

As discussed above and shown in example 1, results indicate that HU-211 elicits neuroprotective activities that could not be displayed by MK-801 although both drugs are non-competitive NMDA antagonists and can protect neurons from excitotoxicity via binding to identical sites located in the NMDA linked ion channel. It is evident that HU-211 can protect neurons from damage induced by a variety of drugs, probably via more than one mechanism of action. The broader spectrum of neuroprotective activity displayed by HU-211 is obviously of great advantage.

PHYSIOLOGICAL EXAMPLE 3

The neuroproteotive effect of HU-211 on permanent focal ischemia (rat MCAo)

The neuroprotective effect of HU-211 was assessed in a model of permanent focal ischemia using rats in which the middle cerebral artery was electrically coagulated. In this model, the primary damage caused is not amenable to pharmacological intervention. Improvement in the outcome is expected in terms of reduction in the penumbra of secondary damage which can be contained to the immediate vicinity of the MCA. Thus, successful intervention will reduce the total infarct volume.

PROCEDURES

Animals (Sprague-Dawley rats weighing 300–400 g) were fasted overnight but were allowed free access to water. Anesthesia was induced with 4% halothane, 70% nitrous oxide and a balance of oxygen and was maintained with 2% halothane and 70% nitrous oxide during the surgical procedures. Atropine sulfate (0.04 mg, i.p.) was injected. The right femoral artery and vein were cannulated with PE-50 polyethylene catheters for monitoring of arterial blood pressure and blood gases, and for the administration of drugs. Rats were than intubated endotracheally, immobilized with pancuronium bromide (initial dose, 0.6 mg/kg; additional dose, 0.2 mg/kg, i.v.), and were mechanically ventilated. The animals were fixed in a stereotaxic frame (Stoelting, Ill.). Blood gases (ABL 30 system, Radiometer, Copenhagen), plasma glucose and lactate (Glucose/Lactate Analyzer Model 2300 STAT, YSI, Ohio) were monitored 30 min prior to the administration of HU-211 or vehicle during ischemia (30 min after MCAo, i.e. 60 min after drug administration). Physiological variables were kept within normal limits.

MCA exposure, brain temperature monitor and CBF monitor. The right MCA was exposed by the method of Tamura et al. (Tamura et al., J. Cereb. Blood Flow Metab., 1: 53–60, 1981). In brief, the cranial vault and the right lateral surface of the skull were exposed via a longitudinal skin incision between the eye and the ear. The zygomatic arch was removed. A burr hole (1.5 mm in diameter) for the brain temperature probe was made above the right parietal cortex by means of a high-speed min-drill (Nihon-Seimitsu Kikai Kogyo K. K., Japan) under an operating microscope (Carl Zeiss, Germany); the field was irrigated frequently with cooled saline to avoid thermal damage. Brain temperature was monitored with a thermocouple probe (CN 9000, Omega), which was inserted into the cerebral cortex (approximate coordinates, 4 mm lateral to the bregma, 2 mm depth from brain surface). Brain temperature was maintained between 35° –36° C. by means of a small heating lamp placed 20 cm over the head. Another burr hole (2 mm lateral to the burr hole for the temperature problem, 2 mm in diameter) was made in the lateral surface of the temporal bone to permit continuous CBF measurement by laser-Doppler flowmetry (P433-3, Vasamedics). This probe was connected to a perfusion monitor (LaserFlo BPM 403 A, Vasamedics). This position of the probe was determined based upon previous studies (Duverger and MacKenzie, *J. Cereb. Blood Flow Metab.* 8: 449–461, 1988; Shiraishi, Sharp & Simon, *J. Cereb. Blood Flow Metab.* 9: 765–773, 1989; Tyson et al., *Ann. Neurol.* 15: 559–567, 1984) using the same proximal MCA occlusion model in Sprague-Dawley rats. A temporal burr hole was then made in the retro-orbital region to permit clipping of the MCA and the dura mater covering the MCA was opened.

Steady state monitor, drug administration and MCAo. Following these surgical procedures, the inspired halothane was discontinued to avoid the effect of halothane on systemic blood pressure and CBF. Anesthesia was maintained with 70% nitrous oxide and 30% oxygen. Thirty minutes after discontinuation of halothane, measurement of the preischemic physiological variables, CBF, MAP, and pulse rate was begun. Steady-state baseline values were recorded before the administration of HU-211 or the vehicle, and CBF was expressed as a percentage of the average of 6 baseline measurements taken every 5 min prior to the administration. Because ambient light interferes with the flow reading, the heating lamp was turned off for 30 sec at the time of each CBF recording. Brain temperature did not decrease below 35° C. during this period. To detect the effect of HU-211 on CBF and MAP, these variables were measured every 15 min after the administration of HU-211 or the vehicle.

After 30 min of pre-ischemic data sampling, HU-211 (11 mg/ml, 20 mg/kg i.p.) or the same amount of vehicle was administered. Thirty minutes after the drug administration, the proximal portion of the right MCA was electrocoagulated and severed.

Brain perfusion, pathological study: Brains were perfusion-fixed for pathological examination 3 days following the ischemic insult. The rats were deeply anesthetized with pentobarbital and perfused transcardially with physiological saline (5 min) and then with FAM (a mixture of 40% formaldehyde:glacial acetic acid:methanol, 1:1:8 by volume, 20 min) at a pressure of 120 mmHg. The head was immersed in FAM for at least 24 hours; the brain was then removed and kept in the same fixative for 7 days. The brains were cut coronally and embedded in paraffin. Brain sections 10 mm thick were prepared at 200 mm intervals and were stained with hematoxylin and eosin. For a morphometric study, ten coronal sections were selected at defined anatomic levels (Osborne et al., 1987). Each section was viewed at low power (10×), and the cortical infarct was traced onto paper using a camera lucida microscope attachment. Each drawing was then retraced onto a digitizing tablet interfaced to a computer, which calculated infarcted areas at each coronal level. Infarct volume was computed by numerical integration of sequential infarct areas.

Stereotaxic coordinates (mm) of levels 1–10 are: 1=12.13; 2=10.05; 3=8.92; 4=7.19; 5=6.06; 6=5.15; 7=3.75; 8=2.18; 9=1.02; 10=–0.48 anterior to the interaural line.

RESULTS

Animals whose physiological variables could not be kept within normal limits, or which had uncontrollable bleeding, were excluded from analysis. A total of twenty-nine rats were used. Twenty rats were operated on without uncontrollable bleeding and met the physiological criteria. One rat out of 20 was discarded because the pathological finding disclosed no cerebral infarction. The absence of infarction means the failure of MCAo.

Figure 4:
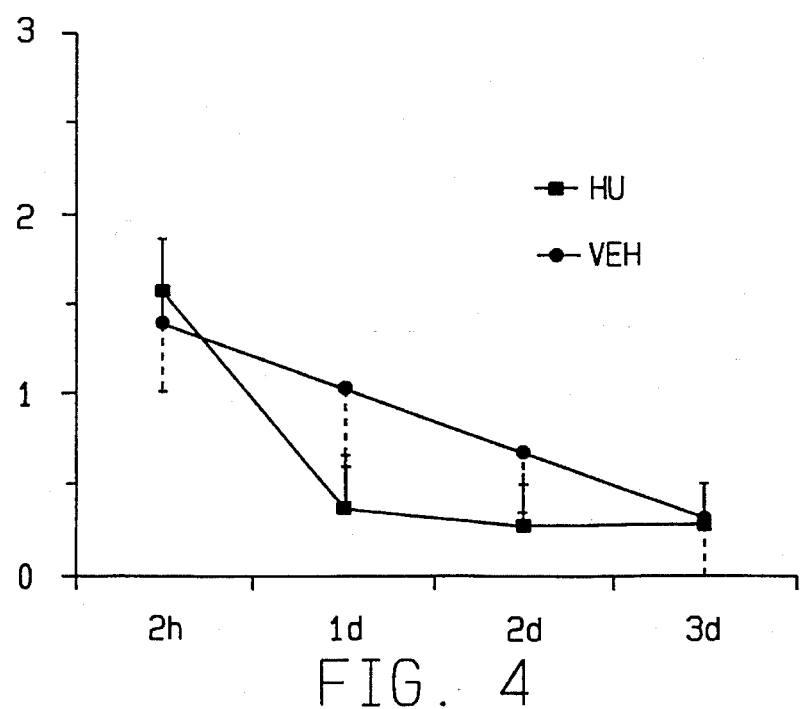
FIG. 4 shows the improvement in neurological scores after middle cerebral artery occlusion is accelerated by HU-211.
Figure 5A:
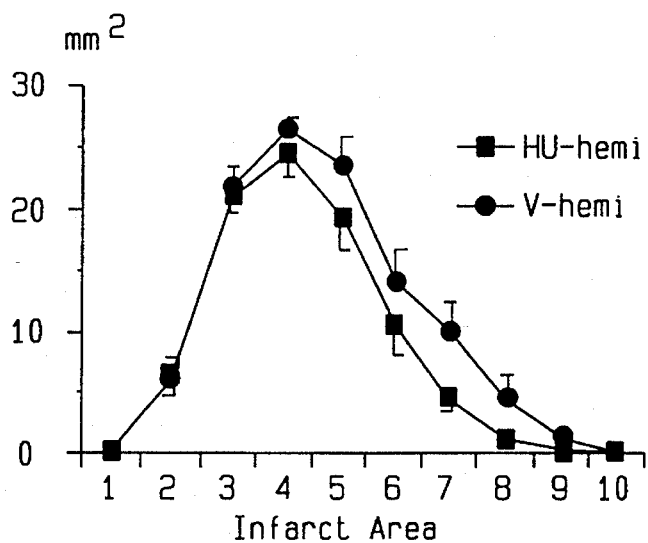
FIGS. 5A–5C show decreased infarct area caused by middle cerebral artery occlusion after HU-211 treatment.
Figure 5B:
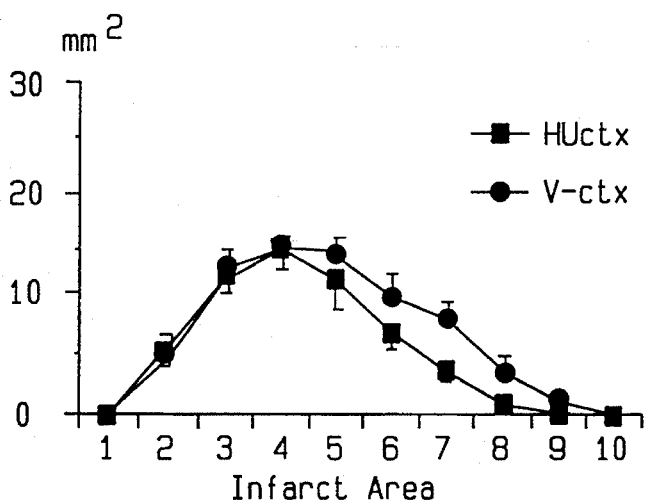
Figure 5C:
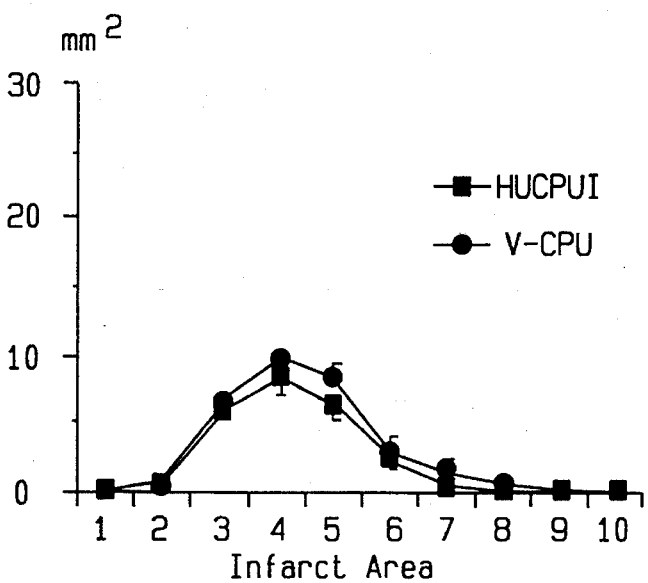

As can be seen in FIG. 4, the neurological scores at 1$d$, 2$d$ and 3$d$ after MCAo were significantly improved compared with the neurological score of 2 h, in the HU-211 treated group. The improvement in the HU-211 treated group was significantly accelerated compared to vehicle-treated controls. More revealing is the analysis of infarct area presented in FIG. 5. At levels between 4 and 8, the infarct volume of HU211 treated animals was significantly reduced. This indicates that HU-211 is effective in significantly reducing the penumbral damage which occurs outside the region consistently involved in direct damage due to the MCA occlusion.

PHYSIOLOGICAL EXAMPLE 4

The effect of HU-211 on cerebral edema in a rat model of head trauma

The cerebroprotective effect of HU-211 was assessed in a model of head trauma (HT) in rats. Injury was induced in anesthetized rats by a weight-drop device followed by a recovery period of up to 48 hours. This type of trauma produces brain edema (i.e. increase in water content, decrease in specific gravity in the brain), breakdown of the blood brain barrier (BBB) and clinical dysfunction. The clinical status of the rats was evaluated 1, 24 and 48 hours after injury along with measuring the extent of cerebral edema. The neurological deficit, assessed by a set of criteria termed the Neurological Severity Score (NSS), is maximal at 1 hour after the initiation of head trauma. The NSS slowly decreases over time from the initiation of HT, with the gradual spontaneous recovery of the rats.

HU-211 significantly reduces edema formation and BBB disruption when given before (30 min), immediately after HT (0 min) or even 1 and 2 hours after HT. This effect was similar regardless if the active ingredient was given into the brain (i.c.v.) or parenterally (i.p. or i.v.). The doses required for significant neuroprotection depend on the mode of administration and range from 0.5–20 mg/kg. It is also important to note that the NSS, mainly specific motor function (e.g. beam-walk and balance) improved significantly upon administration of HU-211. In fact, even one dose of HU-211, given 1 hour after the impact, effectively reduced edema and improved the clinical outcome measured 48 hours after HT (Shohami et al., *J. Neurotrauma* 10: 109, 1993)

Experimental procedure: The model was described in detail by Shapira etal., *Crit. Care Med.* 16: 258–265, 1988. Rats were subjected to head trauma (HT) by a weight-drop device and surviving rats were followed up after one week. During that period they had free access to food and water, and were kept 2–3 rats to a cage. At any predesignated time (15 min, 1, 4, 24, 48 hrs, 4, 7 days) rats were sacrificed. Their brains were then rapidly removed and cortical tissue taken to determine water content, ions and the metabolites of interest at any particular metabolic cascade studied. During the recovery period, the clinical status was evaluated by a set of criteria (NSS).

Trauma induced a significant decrease in specific gravity (SG) of brain tissue and increase in water content following head injury. Edema developed since more water accumulates in either the extracellular (vasogenic) or intracellular (cytotoxic) spaces. The methods employed to determine edema are based on linear gradient columns of bromobenzene and kerosene (for SG) and for water content on drying the tissue in a desiccated oven. Tissue pieces (20 mg each) were placed on top of the column and the SG calculated from the equilibrium position in the column, using a standard curve.

Animals were given chloral hydrate (350 mg/kg i.p.) and placed in a 4.7 Tesla magnet 30 minutes after the trauma for a 10 min T2 weighted scan (TR=2.5 sec), TE=55 msec, Slice thickness=1 mm, center to center slice separation=1.2 mm, 128×256 matrix, FOV=5 cm). One hour after trauma, rats received an i.v. injection of HU-211 5 mg/kg in emulsion (N=9), or the appropriate vehicle (N=11). The scan was repeated 24 hours post-trauma. The extent (volume) of initial damage to the brain was calculated from the volume difference between the right and left hemispheres. The volume of edema 24 hours later was calculated from the area of hyperintense regions (besides ventricles) on all the slices where such regions were observed after thresholding, multiplied by 1.2 mm. The ratio between the volume of initial damage and edema volume was calculated for each individual animal to control for vatiations in initial damage.

RESULTS

Table 2 summarizes the results in two sets of experiments. In the first, HU-211 was administered at a low dose (1.6 mg/kg) directly in to the cerebral ventricle. In the second, it was injected i.p., at 20–30 mg/kg. In both sets of experiments, the drug was given half an hour before, or just after, the induction of trauma and its effect on edema and clinical outcome was evaluated 24 and 48 hours later. The result indicates a significant (p<0.05) decrease in the degree of edema developed after head trauma (HT). About 50% less water was accumulating in the brain as a result of HU-211 treatment to traumatized rats.

TABLE 2

The effect of HU-211 on improving cerebral edema after Head Trauma

| Route of admin. | Dose mg/kg | Time of admin. | Time of evalu. | Percent of SG | Control percent water |
|---|---|---|---|---|---|
| i.c.v. | 1.6 | −30 min | 24 h | 54.7 | 25.0 |
| i.c.v. | 1.6 | 0 time | 24 h | 60.1 | 50.0 |
| i.c.v. | 1.6 | 0 time | 48 h | 66.7 | 49.2 |
| i.p. | 20 | −30 min | 24 h | 65.0 | 60.0 |
| i.p. | 30 | −30 min | 24 h | 60.0 | 62.0 |
| i.p. | 25 | 0 time | 48 h | 63.4 | 62.0 |

The effect of HU-211 was calculated by the percent edema formation, where 100 % was taken as edema in control, non-treated rats. Thus, the reduction in the SG was calculated as follows:

$$SG(\text{sham}) - SG(\text{drug})/SG(\text{sham}) - SG(\text{cont}) \times 100$$

The increase in water content was calculated as follows:

$$\% \, H_2O \, (\text{drug} - \% \, H_2O \, (\text{sham}) / \% \, H_2O \, (\text{cont}) - H_2O \, (\text{sham}) \times 100$$

All results presented in the table are statistically different (p<0.05) from control, traumatized vehicle treated rats.

Figure 6A:
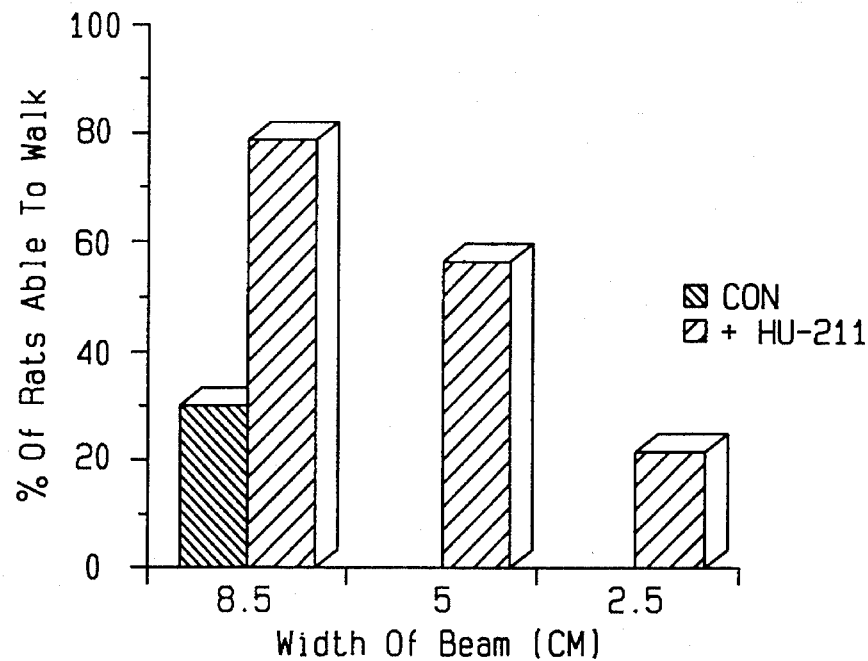
FIGS. 6A and 6B show the effect of HU-211 on motor function of traumatized rats.
Figure 6B:
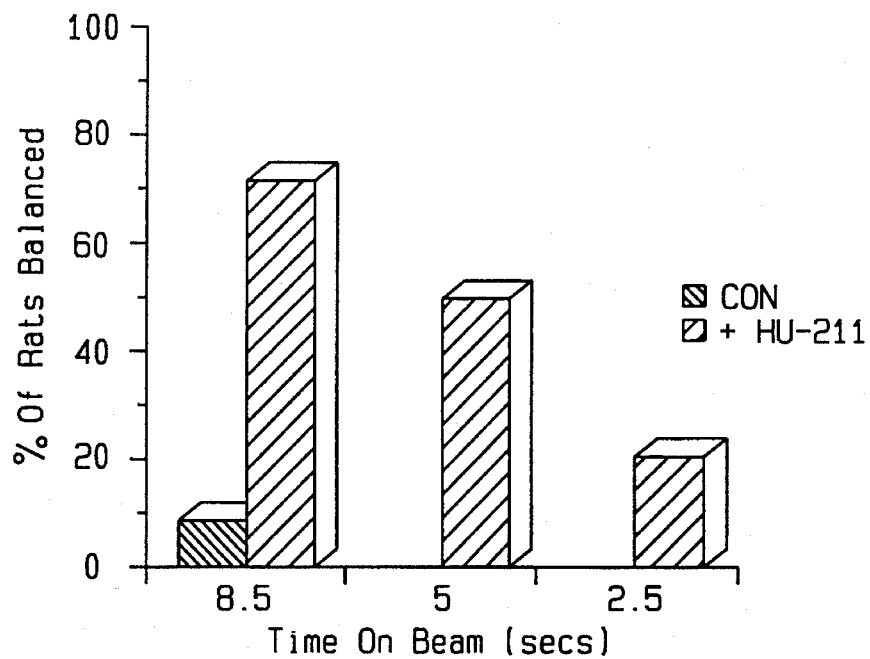
Figure 7A:
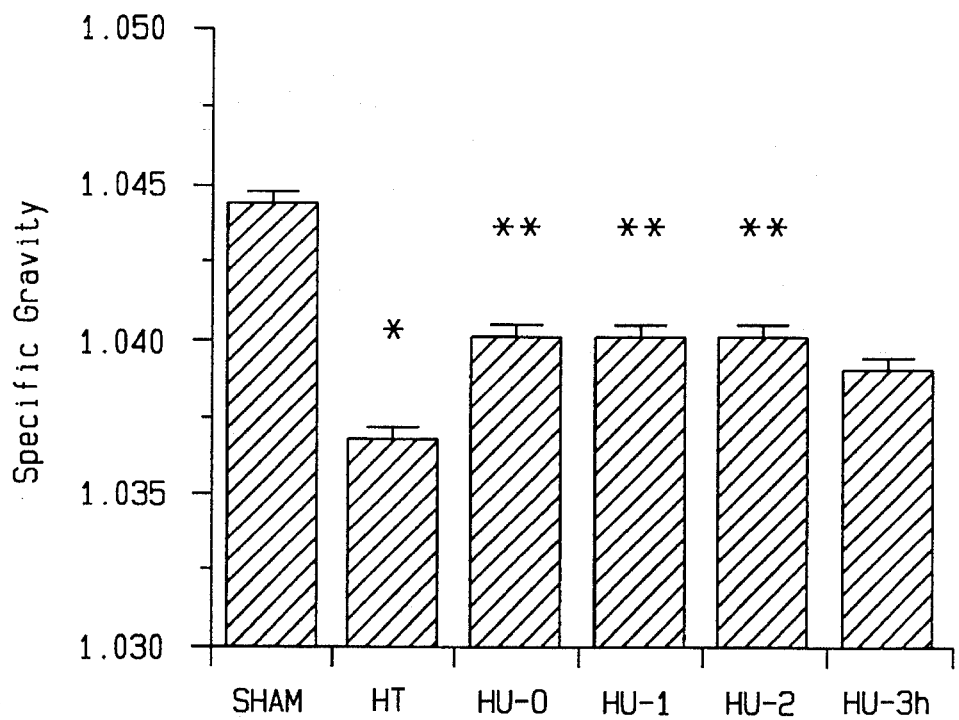
FIGS. 7A and 7B show the reduction of edema formation in traumatized rats treated with HU-211.
Figure 7B:
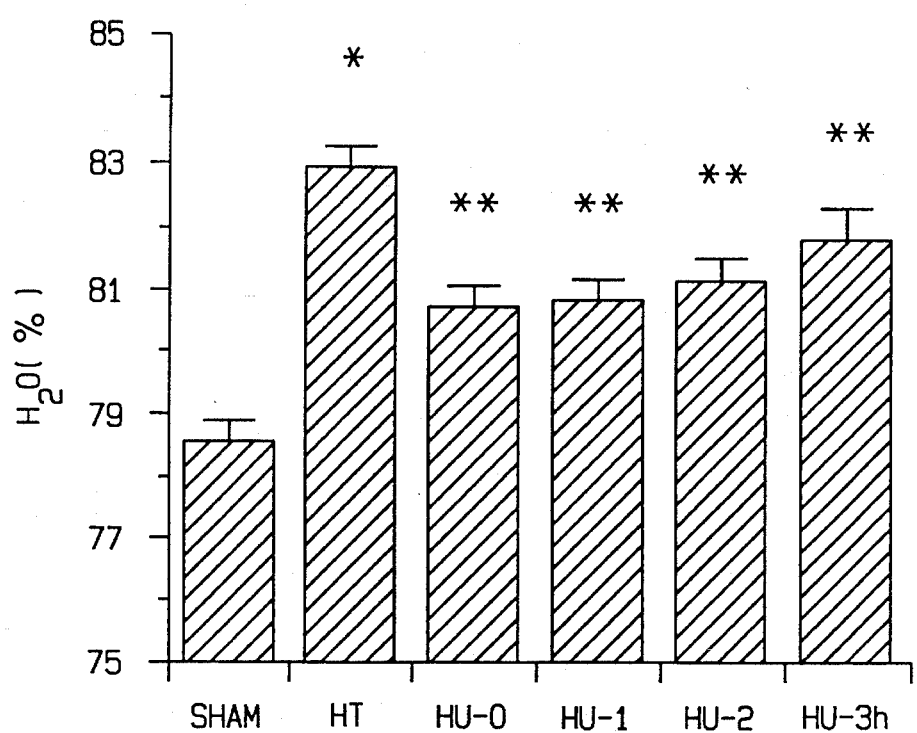
Figure 8:
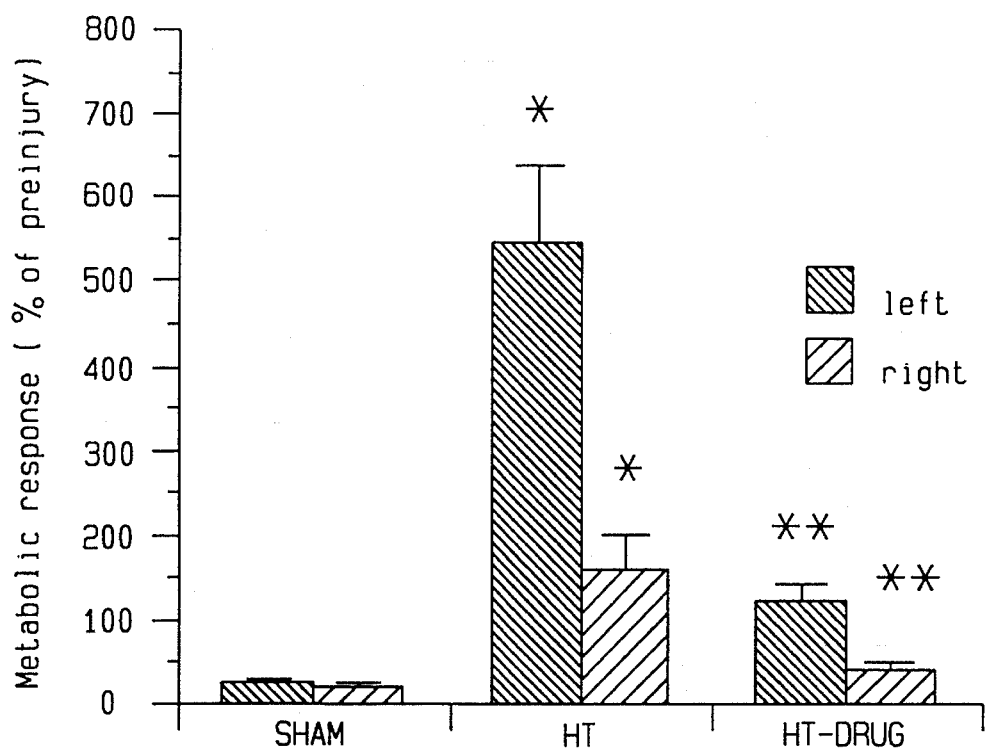
FIG. 8 shows the effect of HU-211 on BBB disruption following head trauma.

After we established the effect on edema, when given 30 minutes prior to, or right after, HT, we investigated the "therapeutic window," namely HU-211, 25 mg/kg i.p. was given one, two or three hours after HT. Its effect on NSS (and on specific motor function) was assessed, as well as the effect on edema and BBB integrity. FIGS. 6–8 summarize the results of these studies. As can be seen, HU-211 was fully effective, even when administered up to 2 h post-injury; at 3 h post-trauma the effect was less pronounced.

MRI analysis of edema. MRI (magnetic resonance imaging) analysis of the results of head trauma enabled us to investigate the effect of HU-211 on the spread of edema in relation to the site and size of initial damage: Animals were scanned 30 minutes after the trauma, injected with HU-211 or vehicle 30 minutes later, and again scanned 24 hours after the trauma. The volume of initial damage was calculated from the difference between the right (uncontused) and left hemisphere, and the volume of the edema was assessed by measuring the hyperintense regions on the brain slices. HU-211 significantly reduced the ratio of edema volume to volume of initial damage, which reflects the spread of edema normalized to the severity of the initial injury.

The volume of brain tissue damage in the experimental animals varied from 15 to 60 µL. The mean volume of initial damage was higher in the HU-211 treated animals (39 µL vs. 24 µL) since vehicle treated rats with large (>45 µL) lesions did not survive. Edema volume, however, was higher in vehicle treated animals (p=0.05) and the ratio of edema to initial damage in individual rats was significantly lower in the HU-211 treated group: mean±sem vehicle, 5.95±1.6; HU-211 1.6±0.55; p<0.03, Student's t-test, two tailed.

CONCLUSION

Severe head injury, or cerebral ischemia, is associated with a high mortality rate (exceeding 50%) and poor functional outcome. Despite extensive clinical and experimental research, there are no well-defined therapies for these conditions. There are very few available treatments for brain injury today and the gradual progressive biochemical changes which occur after head trauma can lead to the evolution of permanent neuronal damage. The results clearly demonstrate that the compounds of the instant invention, namely HU-211, possess cerebroprotective properties in a model of closed head injury in rats.

PHYSIOLOGICAL EXAMPLE 5

Beneficial effect of HU-211 on injured rat optic nerves

Injury to nerves of the mammalian central nervous system (CNS) leads to axonal degeneration followed by a loss of cell bodies. Initial degeneration of the injured nerve probably results from direct damage. The physiological and biochemical events that occur in the nerve immediately after injury are probably responsible for the degeneration not only of directly injured axons, but also of those that escaped the primary lesion. Thus, the primary biochemical and physiological events which devastate the spared axons have a critical influence on the long-term functional outcome.

The present study was designed to assess the potential ability of the active ingredients of the present invention, especially HU-211, to attenuate early injury-induced deficits and subsequent physiological manifestations. Early injury-induced deficits were monitored non-invasively in metabolic terms and long-term manifestation in physiological terms.

Monitoring of immediate injury-induced changes offers an optimal means of evaluating the ability of the active ingredient presently claimed (HU-211), like any other potential drug, to circumvent the causes of secondary degeneration, rather than its results. This enables one to find out whether the presently claimed active ingredient (HU-211) or any other tested drugs will facilitate the rescue of axons that escaped primary injury. In all of these studies, the rat optic nerve was used as a model for the CNS. The results are thus applicable to CNS trauma in general and the optic nerve in particular. Moreover, it is specifically indicative of protection against axonal damage and, therefore, is also relevant to spinal cord injuries.

METHODS

Male Sprague-Dawley rats weighing 300–400 g were anesthetized with sodium pentobarbitone (35 mg/kg intraperitoneally). A cannula was introduced into the trachea for artificial ventilation when required. With the animal's head held in place by a head holder, a lateral canthotomy was performed under a binocular operating microscope and the conjunctiva was incised lateral to the cornea. After separation of the retractor bulbi muscles, the optic nerve was identified and a length of 3–3.5 mm was exposed near the eyeball by blunt dissection. The dura was left intact and care was taken not to injure the nerve. The first part of a light guide holder was inserted under the optic nerve and the nerve was gently eased into the light guide canal. The second part was then fixed in place in such a way that the light guide was located on the surface of the optic nerve 1 mm from the site of injury.

Surface fluorometry reflectometry: Monitoring of the intramitochondrial nicotineamine adenine dinucleotide (NADH) redox state is based on the fact that NADH, unlike the oxidized form NAD+, fluoresces when illuminated by light at 366 nm resulting in the emission of blue light with peak emission at 450 nm. The source of the 366-nm excitation light was a 100-W air-cooled mercury lamp equipped with a strong 366-nm filter [Corning 5860 (7–37) plus 9782 (4–96)]. A flexible Y-shaped bundle of optic fibers (light guide) was used to transmit the light to and from the optic nerve, thus making in vivo measurements technically feasible. Excitation light (366 nm) was transmitted through the bundle of excitation fibers to the nerve. The light emitted from the nerve, after being transmitted through a second bundle of fibers, was split in a ratio of 90:10 for measurement of the fluorescent light (90%) at 450 nm and the reflected light (10%) at 366 nm by two photomultipliers connected to a one-channel direct current fluorometer-reflectometer. In order to minimize variations among animals, standard signal calibration procedures were applied at the start of the recordings, as described in detail previously (Yoles et al., *Invest. Ophthalmol. Vis. Sci.*, 30: 3586–3591, 1992). Changes in the fluorescence and reflectance signals during the experiment were calculated relative to the calibrated signals.

Changes in the reflected light were correlated with changes in tissue absorption caused by hemodynamic effects and movements of the optic nerve secondary to alterations in arterial blood pressure and nerve volume. The fluorescence measurements were found to be adequately corrected for NADH redox state measurements by subtraction of the reflected light (366 nm) from the fluorescent light (1:1 ratio) to obtain the corrected fluorescence signal.

Metabolic measurements: Animals, still anesthetized, were allowed to recover for 30 min. from the surgical procedures and were then exposed to anoxic and to hyperoxic conditions. An anoxic state was achieved by having the rat breathe in an atmosphere ventilated by flowing of 100% nitrogen for 2 min., after which it was returned to air. Whenever animals did not return spontaneously to normal breathing, they were twice via the trachea. A hyperoxic state was induced by having the animal breathe 100% $O_2$ for 6–10 min. In order to evaluate the metabolic activity of the optic nerve, the relative changes in reflected and fluorescent light intensities in response to anoxia and to hyperoxia were measured before and after crush injury.

Experimental protocol for metabolic measurements: Using calibrated cross-action forceps (Duvdevani et al., *Res Neurol. Neurosci.* 2: 31–38, 1991), a moderate crush injury was inflicted on the nerve between the eye and the light guide holder at a pressure corresponding to 120 g for 30 sec, as previously described (Duvdevani et al., 1991). In control groups (13 animals), phosphate-buffered saline (PBS) was injected immediately after injury; in the experimental groups (6 animals), HU-211 (20 mg/kg) was injected. Metabolic activity prior to injury was measured in all nerves.

RESULTS

Figure 9:
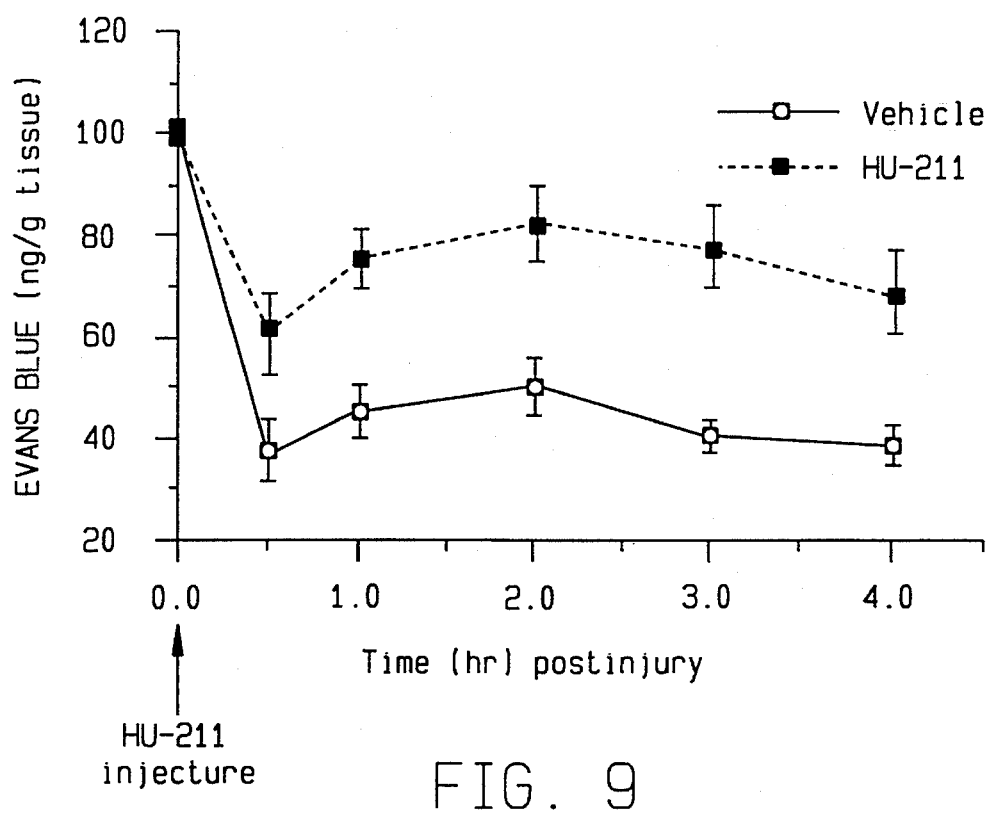
FIG. 9 shows that HU-211 reduces the immediate injury induced deficit in metabolic activity following CNS injury.

FIG. 9 shows the results of a single HU-211 injection (intraperitoneally, 20 mg/kg) at the time of injury on the metabolic activity of the injured nerves. As can be seen, the injury-induced reduction in metabolic activity was partially attenuated by HU-211. The effect was already noticeable within 30 min after the injury. This reduction in the injury-induced deficit lasted at least for the 4 h of the experiment. The effect was statistically significant according to the paired t-test.

To assess the post-injury time period within which the treatment is still beneficial, the experiment was repeated, but HU-211 was injected 2 h after injury. In 3 of the 6 animals examined, a beneficial effect could still be observed.

The HU-211 induced improvement of metabolic activity could be a result of the circumvention of any events which occur in the injured nerves and may eventually lead to $Ca^{2+}$ entrance and axonal degeneration. The overall effect could be a slow-down of degeneration or the rescue of axons not directly damaged by local events in their vicinity.

Assessment of the possible long-term effect of HU211 is achieved by physiological means.

Physiological measurements The experimental setup was as per Assia et al. (1990). Prior to removal of optic nerves for electrophysiological measurement, the rats were deeply anesthetized with 70 mg/kg pentobarbitone. The skin was removed from the skull and the optic nerves were detached from the eyeballs. Subtotal decapitation was performed and the skull was opened with a ronguer. The cerebrum was displaced laterally, exposing the intracranial portion of the optic nerve. Dissection at the level of the chiasm enabled removal of the whole length of the nerve, which was transferred to vials containing fresh, cold Krebs solution, consisting of (in ml): NaCl 125, KCl 5, $KH_2PO_4$ 1.2, $NaHCO_3$ 26, $MgSO_4$ 0.6, $CaCl_2$ 24, D-glucose 11, aerated with 95% $O_2$ and 5% $CO_2$. The nerves were kept in this solution, in which electrical activity remained stable for at least 3–4 hours. After 1 hour of recovery, nerves were immersed in the Krebs solution at 37° C. Electrophysiological recordings were obtained from the nerve distal to the crush lesion, since the nerves were too small to allow measurements on both sides of the crush. The nerve ends were then connected to two suction Ag—AgCl electrodes immersed in the bathing solution. The stimulating pulse was applied through the electrode at the proximal end and the action potential was recorded by the distal electrode. A Grass SD9 stimulator was used for electrical stimulation (2 V, 50 µs). The signal was transmitted to a Medelec PA63 preamplifier and thence to a Medelec MS7 electromyograph and an AA7T amplifier. The solution, stimulator and amplifier had a common ground. The maximum amplitude of 8 averaged compound action potentials (CAPS) was recorded and photographed with a Polaroid camera. The left nerves (uninjured) were used to measure the reference values of normal nerves and to calibrate the crush forceps.

Figure 10A:
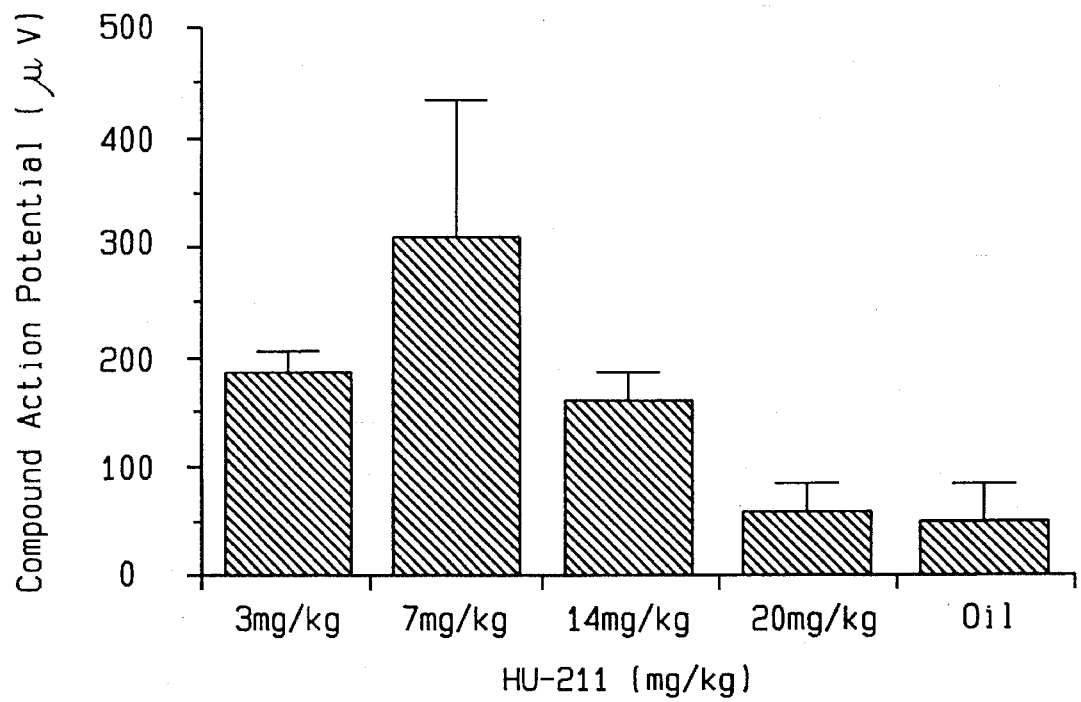
FIGS. 10A and 10B show the long-term beneficial effect of HU-211 manifested electrophysiologically following CNS injury.
Figure 10B:
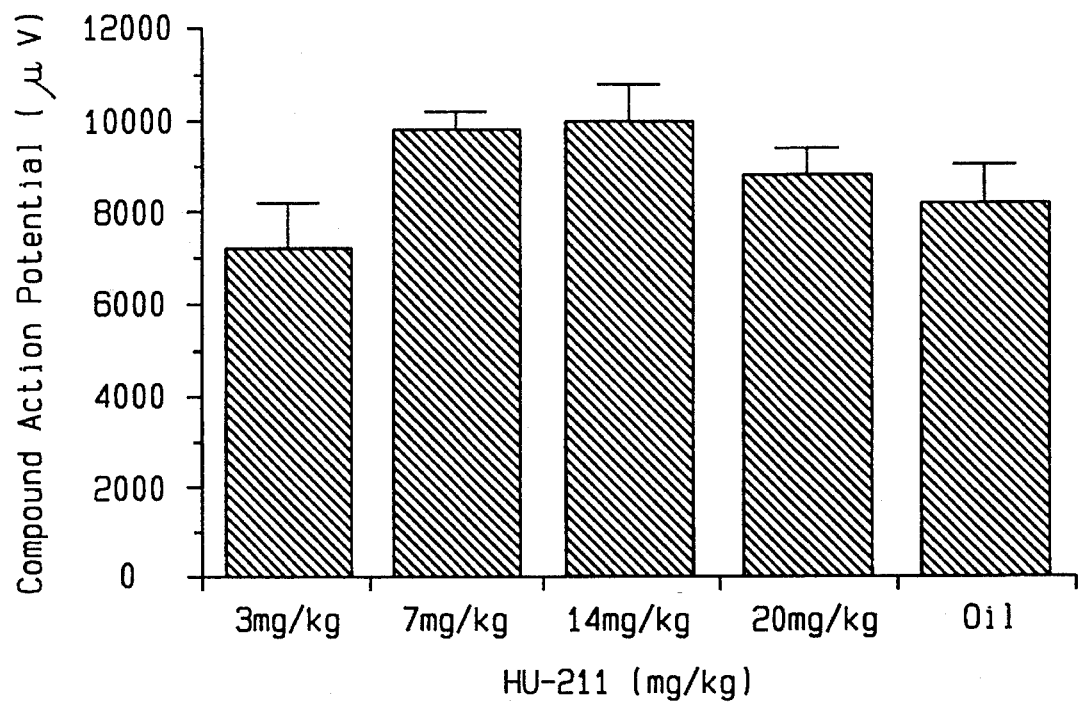

Long-term effect of HU-211. FIG. 10 shows the long-term effect of HU-211 manifested electrophysiologically. HU-211 was injected intraperitoneally at various dosages, immediately after injury. Electrophysiological activity was recorded in vitro 2 weeks after the injury and the drug administration, using suction electrodes.

Figure 11:
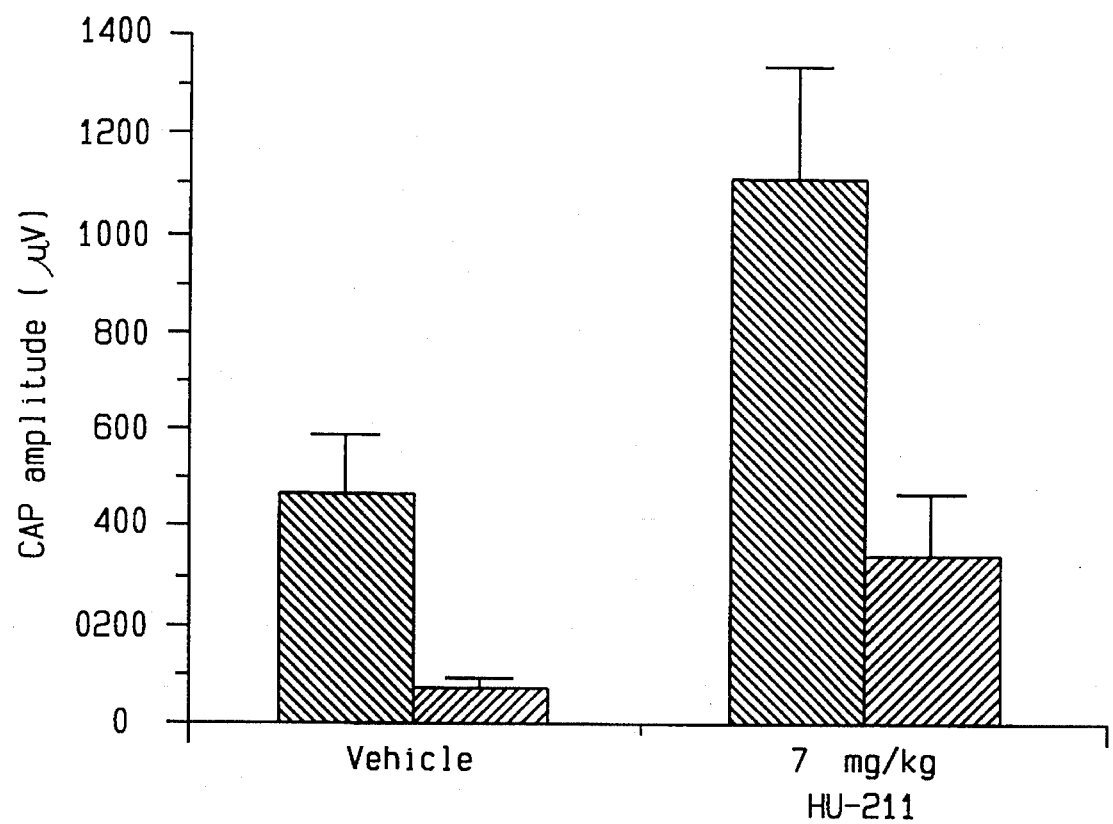
FIG. 11 shows the effect of HU-211 and injury severity on compound action potential amplitude recorded 2 weeks post-injury.
Figure 12:
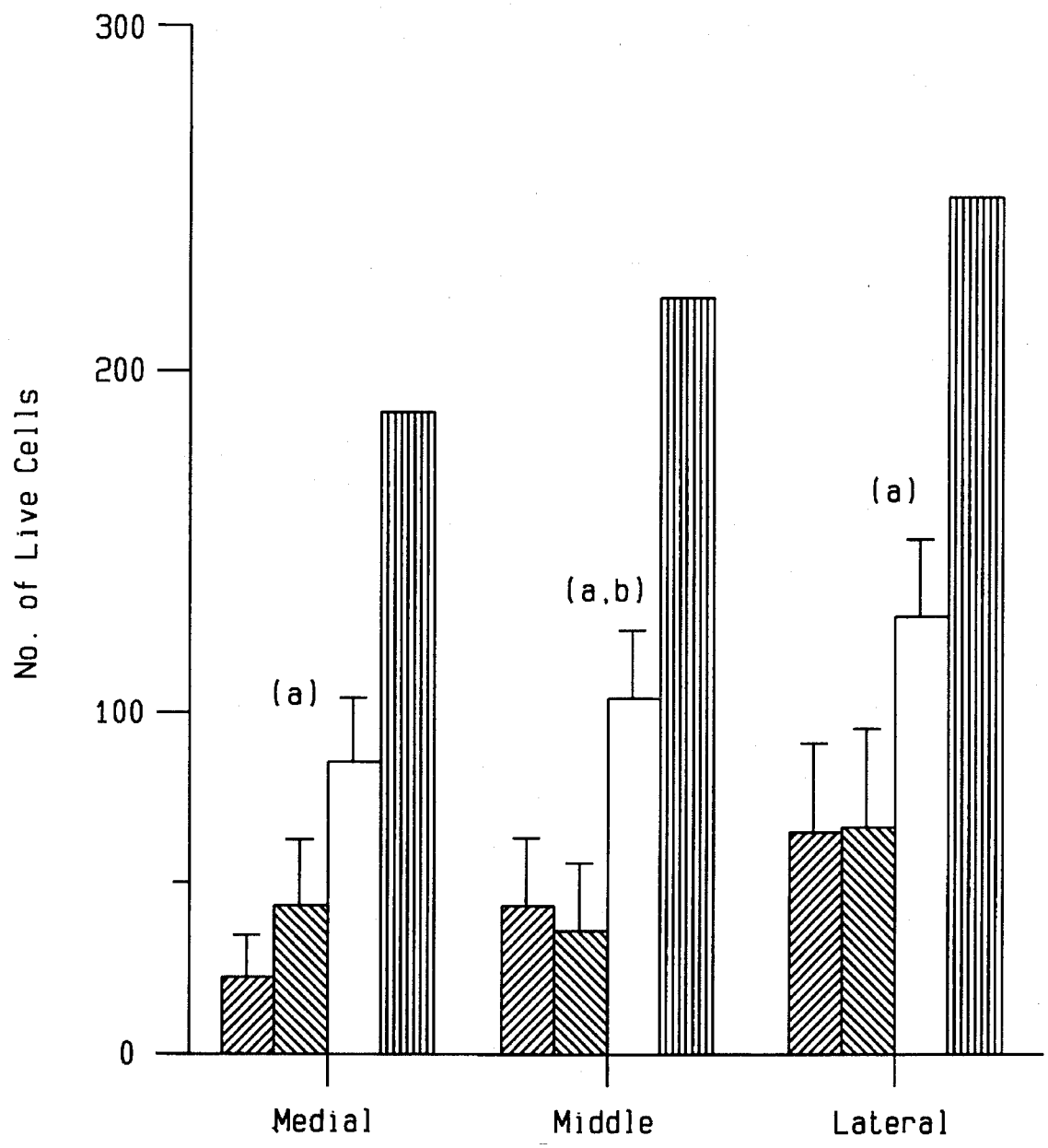
FIG. 12 shows a histopathological evaluation of CA1 sector of the hippocampus of ischemic gerbils.

The various dosages of HU-211 injected at the time of the injury are indicated in FIG. 11. Controls. injured nerves were excised from animals, injected with the vehicle at the time of injury. Already, at 3 mg/kg, the action potential was higher than in control nerves. Maximal physiological activity was observed at 7 mg/kg. At 20 mg/kg there was no effect.

In all animals the contralateral nerves, which were not injured, were used as controls for the physiological measurements and for the treatment. As can be seen, HU211 had no effect on uninjured nerves.

Examination of the shape of the action potential curve (mono- or multicomponents) revealed that HU-211 appears to rescue selectively fast-conducting fibers.

Beneficial effect of HU-211 as a function of injury severity. In all of the above experiments, the crush injury inflicted was of moderate severity. We considered the possibility that the beneficial effect of HU-211 might be more pronounced if the number of injured fibers was lower to begin with, leaving more fibers that escaped primary injury and were vulnerable to secondary degeneration. To test this possibility, we repeated the long-term experiment but inflicted a milder injury. As can be seen, a single injection of 7 mg/kg resulted in a dramatic improvement in the nerve's performance (FIG. 11).

Long-term effect of HU-211 assessed by recording of VEP responses. VEP responses were recorded in an attempt to determine whether HU-211 has any effect on the rescue of fibers and thus on preservation of function. All of these animals had electrodes implanted in the cortex, and then functional recovery was assessed by flashing of light onto the eye with the injured nerve. A positive VEP response was recorded in two of the seven control animals, as compared with five of the eight HU-211-treated injured nerves (Table 3).

From these experimental results, it is evident that the active ingredient of the present invention is effective in treating injuries to the central nervous system and consequently improving the neurological outcome from such injuries.

TABLE 3

VEP responses in injured nerves treated with HU-211, compared with control injured nerves

| Experimental groups | n | Amplitude[a] mean ± S.E. | Latency[b] (msec) mean ± S.E. |
|---|---|---|---|
| HU-211 | 8 | 14.125 ± 2.423 | 29.0 ± 1.558 |
| Vehicle Control | 7 | 7.143 ± 2.423 | 26.5 ± 2.527 |

[a]Analysis of variance: DF = 14, P = 0.0387, F = 5.284

TABLE 3-continued

VEP responses in injured nerves treated with HU-211, compared with control injured nerves

| Experimental groups | n | Amplitude[a] mean ± S.E. | Latency[b] (msec) mean ± S.E. |
|---|---|---|---|

[b]Analysis of variance: DF = 12, P = 0.4029, F = 0.757. No significant difference.

PHYSIOLOGICAL EXAMPLE 6

Neuroprotection by HU-211 in reversible middle cerebral artery occlusion

In this study, Sprague-Dawley rats were subjected to 60 min of temporary middle cerebral artery (MCA) occlusion by insertion of an intraluminal nylon suture retrogradely through the external carotid artery into the internal carotid artery and MCA. The drug (HU-211 in oil, 20 mg/kg i.p.) or vehicle, were administered in a blinded fashion 30 min prior to MCA occlusion. Animals received the following physiological monitoring: intermittent measurement of arterial $PCO_2$, $PO_2$ and pH; continuous measurement of arterial blood pressure; intermittent measurement of blood glucose, and monitoring of temporalis muscle temperature. Animals were allowed to survive for three days. Brains were perfusion-fixed with FAM. Paraffin-embedded coronal sections were stained with hematoxylin and eosin. Infarct areas were measured at 11 coronal levels. At each of these levels, ipsilateral and contralateral hemispheric volume were also measured, and from the latter measurements, an index of hemispheric edema [(ipsi- contra)(contra)] was computed.

Experimental design. The initial design was a randomized one, in which the experimenter was blinded as to whether drug or vehicle was being given, and an attempt was made to generate approximately equal numbers of drug- and vehicle-treated animals. It became apparent that many animals failed to survive, and that they were, for the most part, vehicle-treated rats. Thus, additional animals were added to the series, and these were predominantly drug-treated, so as to obtain eventually equal numbers for statistical analysis. The final number of animals studied in this series is as follows:

TABLE 4

| Animals surviving for histopathology | HU-211 group, n = 7 |
| | Vehicle group, n = 7 |
| Non-surviving animals | HU-211 group, n = 1 |
| | Vehicle group, n = 7 |

RESULTS

Survival: These are indicated above in Table 4. These data were analyzed by Fisher's exact probability test, which yielded a p<0.1 suggesting a significant trend toward improved survival in HU-treated animals.

Physiological data: Essentially, there were no important differences in mean arterial blood pressure or blood gases among surviving animals treated with HU-211 or vehicle, or non-surviving animals. Similarly, there was no difference in head temperature. One should note that in these spontaneously breathing animals, arterial $PCO_2$ tended to be somewhat elevated in all groups.

Infarct and edema volumes: Individual and mean data are presented in Table 5. It is apparent that, with 60 min MCA occlusion, there is an extremely broad range of infarction.

Nonetheless, there is a trend toward an 18% reduction in mean infarct volume with HU-211, as well as a 31% reduction in edema volume.

The data presented show a significant trend toward improved animal survival with HU-211 treatment, and a moderate reduction in infarct volume in surviving animals. As noted above, if all animals had survived, and if one assumes that infarcts in the dying animals were larger than in the survivors, the data may have shown a stronger tendency for HU-211 to reduce infarct volume. That is, HU-211 may both increase survival in animals with very large infarcts, and at the same time, reduce infarct volume. These results demonstrate the therapeutic potential of HU-211 in transient focal ischemia, which is considered a model of stroke in humans.

TABLE 5

| | Infarct and edema volumes | | |
|---|---|---|---|
| | Animal No. | Infarct (mm$^3$) | Edema (mm$^3$) |
| HU-211 | 1 | 6.2 | 13.0 |
| | 2 | 30.9 | 11.9 |
| | 3 | 32.2 | −1 d |
| | 4 | 74.0 | 47.9 |
| | 5 | 70.8 | 33.2 |
| | 6 | 127.2 | 30.1 |
| | 7 | 277.9 | 57.8 |
| Mean | | 89.5(82%)* | 27.5(69%)* |
| Vehicle-treated | 1 | 0 | 20.2 |
| | 2 | 20.1 | 19.9 |
| | 3 | 3.6 | 13.7 |
| | 4 | 27.1 | 31.9 |
| | 5 | 33.6 | 16.6 |
| | 6 | 295.5 | 125.3 |
| | 7 | 388.1 | 51.5 |
| Mean | | 109.7 | 39.9 |

*% of vehicle control

PHYSIOLOGICAL EXAMPLE 7

Neuroprotection against cerebral ischemia in gerbils

The compounds of the present invention were tested for their ability to prevent neurological damage in gerbils exposed to bilateral common carotid artery occlusion.

Mongolian gerbils (male), 65–70 gr (Tumblebrook Farm) underwent the ischemic procedure while anaesthetised with equithisine.

Common carotid arteries (CCA) were isolated and 3–0 silk suture material was positioned loosely round them. The tips of each loop were tied together, and the suture material was buried beside the trachea. The ventral neck incision was then sutured. In the following day, they were lightly anaesthetised with ether, the neck skin wounds were opened and both CCA were occluded for 10 minutes using small artery clips. During the ischemia and until the animals recovered (regaining righting reflexes), they were maintained in a warm state (36.5° –37.5° C. rectal temperature). Thirty minutes following onset of ischemia, animals were reanaesthetised (ether) and the appropriate drug was administered i.v. via the femoral vein.

Clinical evaluation. Three to 5 hours later, animals were observed for their clinical appearance using the Rudolphi method (Rudolphi et al., Cereb. Blood Flow Metab. 7: 74, 1987). This was done every 24 hours, for the entire 96-hour period. At the end of this period, animals were anaesthetised (equithisine) and perfused transcardially with 10% formaldehyde solution.

TABLE 6

Neurobehavioral scores in stroke model in gerbils
(normal score, 0)

| Neurological behavior | Score(s) |
|---|---|
| Normal | 0 |
| Sleepy/lethargic | 1 |
| Hyperactive | 2 |
| Circling/Ptosis | 3 |
| Jumping | 4 |
| Tossing seizures/Ophistolonus | 5 |
| Tonic convulsion | 6 |
| Coma, weak pain response | 7 |
| Coma, no pain response | 8 |
| Death | 9 |

Modification of Rudolphi's Clinical scoring method.

Histopathological evaluation. Brains were removed and stored for one week. Then, 5 µm sections were cut from the area of the dorsal hippocampus, stained with H&E and cresyl violet, and evaluated according to the following system. The number of viable pyramidal cells in the medial, middle and lateral CA1 subfield of the hippocampus we counted under ×400 magnification, along 0.4 mm in both sides.

The study paradigm was (n=10): untreated animals, vehicle treated animals (SME, 4 ml/kg i.v.); and animals treated with the test drug (8 mg/kg I.V.)

Statistics. Neuroclinical appearance was analyzed using Wilcoxon Rank Sum Test. The histopathological evaluation was analyzed using One-Way ANOVA followed by Duncan's Test.

RESULTS

Behavioral study: As can be seen from Table 7, the clinical status of the HU-211 treated group showed a significantly better performance (low score, mean 2.1) compared to the vehicle treated group (mean 4.0) and untreated group (mean 8.6). The HU-211 group showed far fewer severe signs (only one animal had severe, i.e. 5–8, scoring symptoms) compared to the control groups. Five animals from the HU-211 treated group showed no signs at all (compared to none from the untreated group and 1 from the vehicle treated group).

Also, the decreased mortality rate (Table 8) showed a strong trend of ischemia (stroke) protection in the HU-211 treated animals compared to the control groups.

Histopathological evaluation: The results demonstrate (Table 9) significant differences in CA1 hippocampal degeneration, due to ischemic insult, among the different treatment groups. The untreated and the vehicle treated groups were damaged far more severely than the HU-211 treatment group.

All animals showed some damage compared to naive controls (FIG. 13), however significantly more live cells were preserved in the HU-211 treated animals.

TABLE 7

Gerbil ischemia model improved clinical outcome
after administration of HU-211
(8 mg/kg i.v., 0.5 h post-insult)

| Treatment | Average Neurological Score ± S.E.M. |
|---|---|
| HU-211 | 2.1 ± 0.7* |
| Vehicle | 4.0 ± 1.3 |

TABLE 7-continued

Gerbil ischemia model improved clinical outcome
after administration of HU-211
(8 mg/kg i.v., 0.5 h post-insult)

| Treatment | Average Neurological Score ± S.E.M. |
|---|---|
| Untreated control | 8.6 ± 2.9 |

*HU-211 vs. untreated p < 0.01

TABLE 8

Mortality rate in different treatment groups
after 10 mins bilateral CCA occlusion in Mongolian gerbils

|  | Untreated n = 10 | Vehicle n = 10 | HU-211 n = 10 |
|---|---|---|---|
| % dead | 30 | 20 | 0 |

TABLE 9

Gerbil ischemia model.
Improved histopathological outcome after administration HU-211
(8 mg/kg i.v., 0.5 h post-insult)

| Treatment | CA1 hippocampal cell count |
|---|---|
| HU-211 | 102.8 ± 20 |
| Vehicle | 34.9 ± 17.6** |
| Untreated | 42.1 ± 21* |

*HU-211 vs. untreated p < 0.02
**HU-211 vs. vehicle p < 0.05

As can be seen from the above tables, a significantly better clinical performance is observed after treatment with the active ingredient of the present invention, compared to vehicle and untreated controls.

The active ingredient of the present invention improved both neurological and histopathological outcomes of global ischemia in the Mongolian gerbil model. The two control treatments demonstrated a similar performance: severe neurological deficit and similar CA1 hippocampal degeneration.

PHYSIOLOGICAL EXAMPLE 8

Neuroprotection by HU-211 in 4 VO model in rats

The 4-vessel occlusion (4 VO) rat model is often used as an animal model for brain ischemia, because it is relatively easy to produce and shows good reproducibility. Transient but severe global or forebrain ischemia, which occurs clinically in patients successfully resuscitated from cardiac arrest and experimentally in some animals models, causes irreversible injury to a few, specific populations of highly vulnerable neurons.

In our study, HU-211 in hydroxypropyl-β-cytodextrin (HPCD) protects against neuronal damage caused by transient, severe forebrain ischemia in rats. The 4 VO model is a more severe model of ischemia compared to the gerbil model and is usually not responsive to treatment. The effect of HU-211 and compounds of the instant invention in this model demonstrate the utility of these compounds as neuroprotective agents.

MATERIALS AND METHODS

Sprague-Dawley male rats (180–400 g) supplied by Anilab (Hulda, Israel) were used in this study. They were anesthetized using Pentothal (Abbott, Italy) for induction, with Halothane (ICI Pharmaceuticals, England), in a mixture of 70% $N_2$ and 30% $O_2$ for maintenance.

Two test materials were used: 45% HPCD, in water, for vehicle treatment (4 ml/kg) and HU-211 (8 mg/kg) in 45% HPCD, in water, prepared at Pharmos Ltd. (Rehovot, Israel). Animals underwent four-vessel occlusion model (4 VO) according to Pulsinelli et al. (ref) 1982: A two-stage operation was performed:

(1) On the first day the vertebral arteries were occluded. A midline skin incision was performed above the spinal cord behind the skull occipital bone. Muscles were separated and cut until the C1 vertebra was isolated. The alar foramina are located and the vertebral arteries are coagulated via the alar foramina. Muscles and skin and closed in two layers. On the same day, the common carotid arteries (CCA) are isolated through a central neck midline incision. A loose suture material is positioned around them and the skin is closed.

(2) On the second day the CCA are occluded. The animal is anesthetized lightly (ether), the skin is opened and CCA are closed for 20 min with arterial clips. Animals were fasted overnight between the two stages of the study (water was allowed). Loss of righting reflex is the principal criterion for assuring severe forebrain ischemia in the 4 VO model in the rat. Therefore, animals not showing this sign were not included in the study. Animals were assigned at random to a treatment group on the day of CCA occlusion.

Test material was administered i.v. 15 min before the onset of CCA occlusion. HU-211 was administered at a dose of 8 mg/kg or the same volume of vehicle (HPCD) was given (4 ml/kg).

Four "treatment" groups were used:
(a) Sham animals underwent occlusion of both vertebral arteries, without common carotid arteries occlusion.
(b) Control untreated animals—occlusion of both vertebral and common carotid arteries.
(c) HPCD (vehicle) treated controls—occlusion of both vertebral and common carotid arteries, animals treated with HPCD 15 min before CCA occlusion.
(d) HU-211 (in HPCD)—occlusion of both vertebral and common carotid arteries, animals treated with HU-211 15 min before CCA occlusion. Body (rectal) temperature was maintained between 38°–38° C. Animals were monitored for their clinical appearance at the following time periods:
(i) before vertebral occlusion
(ii) before CCA occlusion
(iii) 5 hours after CCA occlusion
(iv) 24 hours after CCA occlusion
(v) 48 hours after CCA occlusion
(vi) 72 hours after CCA occlusion

TABLE 10

Neurological examination - grading scale for rats
(four vessel occlusion global ischemia model)

| Test | Normal score | Normal total | Deficit |
|---|---|---|---|
| Equilibrium on horizontal bar | 1 for each paw | 4 | 0 |
| Grasping reflex | 1 for each paw | 4 | 0 |
| Righting reflex: | | | |
| Righting of head when | 1 for | 2 | 0 |

TABLE 10-continued

Neurological examination - grading scale for rats
(four vessel occlusion global ischemia model)

| Test | Normal score | Normal total | Deficit |
|---|---|---|---|
| tilted | each side | | |
| Righting when laid on back | 1 | 1 | 0 |
| Spontaneous motility | 2 | 2 | 1 (walk on digits) or 0 (no walking) |
| Absence of forelimb flexion | 1 | 1 | 0 (present) |
| Absence of thorax twisting | 1 | 1 | 0 (present) |
| Absence of ptosis | 1 | 1 | 0 (present) |
| Global neurological score (normal) | | | 16 |

RESULT

Figure 13:
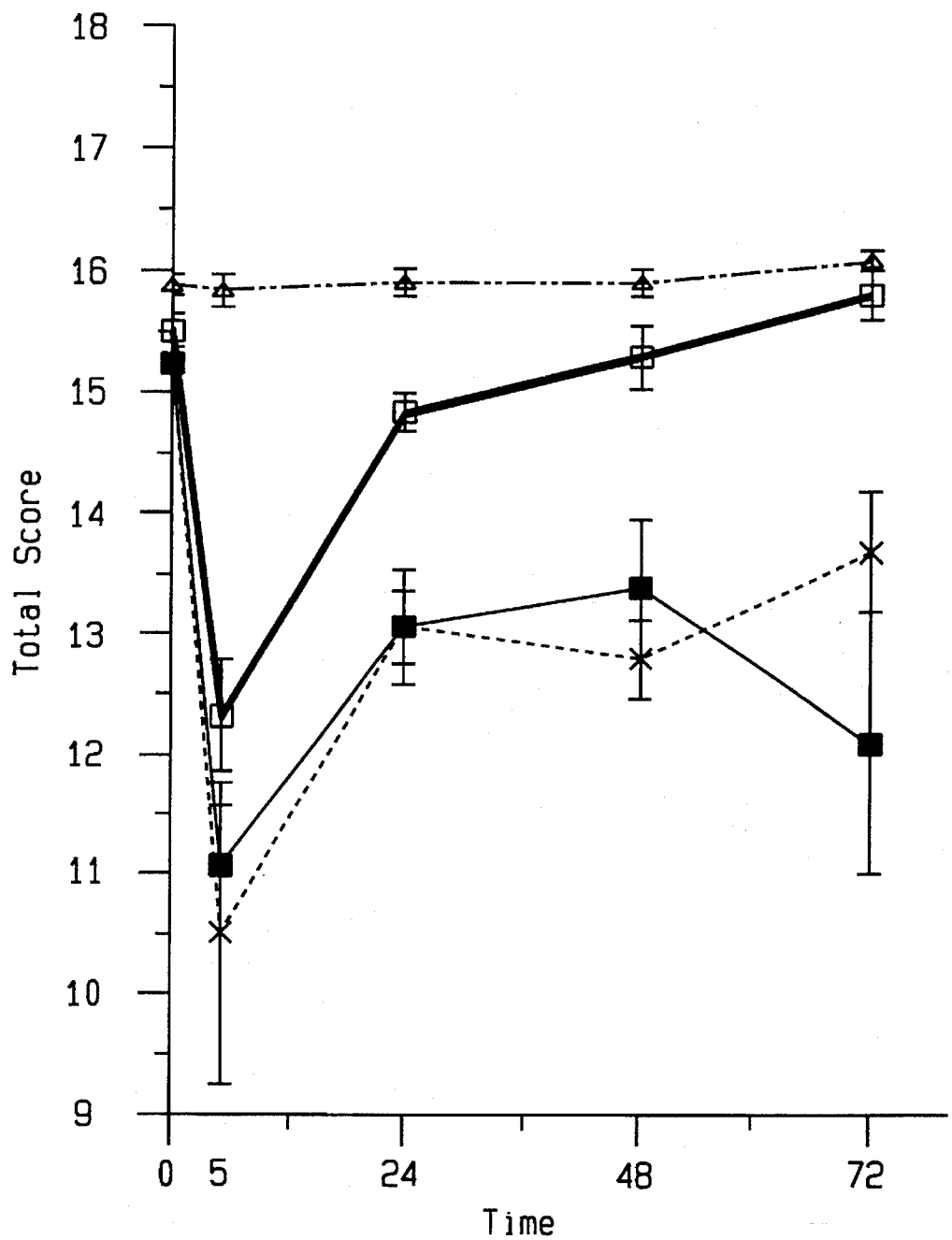
FIG. 13 shows the effect of HU-211 on neurological severity scores in animals subjected to global ischemia.

As the results indicate in FIG. 13, the vehicle alone is indistinguishable from the control (ischemic untreated) group. The HU-211 treated group is significantly better than the control ischemic untreated or vehicle only groups, and is remarkably indistinguishable from sham operated animals by 72 hours after the initial surgical insult. At 48 hours post-insult, the HU-211 treated group was already not statistically different from the sham operated group. These tests were conducted with 17 animals per group. The data shown represent overall neurological score improvement rates (i.e. difference between normal score which is 16 and the score at the time of examination). Note that in the Duncan Multiple Range Test for each time increment where a measurement was taken, the difference between the sham group and the HU group decreased, eventually reaching zero after 72 hours. Therefore, HU-211 and compounds of the instant invention may be useful in the management of post-ischemic events in patients suffering from neurological trauma. This model is particularly relevant to global ischemia, such as that associated with cardiac arrest.

PHYSIOLOGICAL EXAMPLE 9

Anti-hypoxic effects of HU-211 analogs

Exposure of mice to a hypobaric atmosphere (200 mmHg) results in death within a few minutes in normal, untreated animals. Not only MK-801 but also diazepam and pentobarbital are known to prolong survival of animals in this more general model. HU-211 significantly increased survival time at doses as low as 2 and 5 mg/kg i.p. (in MCT oil). The reduced stereospecific analog of HU-211, denoted HU-251 (Devane et al., *J. Exp. Med.* 2065–2069, 1992) was as effective as 211 in this system.

Hypobaric anoxia was used as a test system for screening the neuroprtoective effects of all novel compounds including HU-211 phosphate and HU-211 succinate. The experimental paradigm was derived from that described by Gotti (Gotti & Depoortere, Congres Circ. Cerebrale, Toulouse, 105–107, 1979). Briefly, mice in groups of 5 were placed in a chamber which was equilibrated at an atmospheric pressure of 200 mmHg (by evacuation via a vacuum pump). The mice were observed until they stopped breathing and the time was recorded for each mouse. The test compounds were administered 45 min before introducing the animals into the chamber. In all cases the experiment was performed in a masked vehicle controlled study to avoid bias on the part of the observer. Each mouse received the test compound dissolved in MCT oil or the appropriate buffered aqueous solution intraperitoneally at a dose of 5 mg/kg, or the vehicle alone. The results clearly indicate a statistically significant increase of survival time in animals pretreated with the compounds of the present invention (Table 11).

TABLE 11

Antihypoxic activity of HU-211 analogs mg/kg i.p.

| Compound tested | Vehicle | Survival (sec) |
|---|---|---|
| Non-treated | — | 123 ± 33 |
| HU-211 | MCT oil | 425 ± 130 |
| HU-251 | MCT oil | 412 ± 94 |
| HU-211 succinate | Tris buffer | 433 ± 58 |
| HU-211 succinate | Bicarbonate buffer | 601 ± 206 |
| HU-211 phosphate | Tris buffer | 471 ± 75 |

The groups included at least five animals per test compound. None of the vehicles had any significant effect on survival.

Although the present invention has been described with respect to various specific embodiments thereof in order to illustrate it, such specifically disclosed embodiments should not be considered limiting. Many other specific embodiments will occur to those skilled in the art based upon applicants disclosure herein, and applicants propose to be bound only by the spirit and scope of their invention as defined in the appended claims.

We claim:

1. A method for treating injuries to the central nervous system by administering to a patient a therapeutically effective amount of a pharmaceutical composition comprising a compound of the formula:

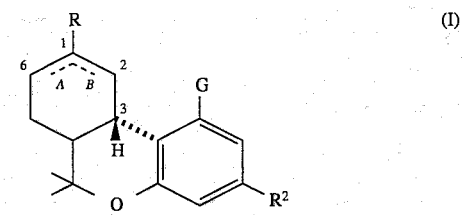

having the (3S,4S) configuration and being essentially free of the (3R,4R) enantiomer, wherein A-----B indicates a 1(2) or 6(1) double bond, R is $C_1$–$C_3$ alkyl or $CH_2OH$, G is —$OR_1$ wherein $R_1$ is hydrogen or —C(O)R''' wherein R''' is a $C_1$–$C_5$ alkyl group, and $R_2$ is (a) a straight or branched $C_6$–$C_{12}$ alkyl group, or (b) —OR'''', in which R'''' is a straight chain or branched $C_5$–$C_9$ alkyl group which may be substituted at the terminal carbon atom by a phenyl group.

2. The method of claim 1 wherein said compound is administered in a manner to protect against excitatory amino acid-mediated neurotoxicity.

3. A method for blocking N-methyl-D-aspartate (NMDA) receptors in a patient which comprises administering to said patient, in a manner calculated to block said receptors in a stereospecific manner, a therapeutically effective amount of a compound of the formula

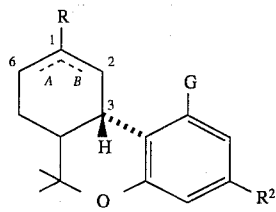

(I)

having the (3S,4S) configuration and being essentially free of the (3R,4R) enantiomer, wherein A-----B indicates a 1(2) or 6(1) double bond, R is $C_1$–$C_3$ alkyl or $CH_2OH$, G is —$OR_1$ wherein $R_1$ is hydrogen or —C(O)R''' wherein R''' is a $C_1$–$C_5$ alkyl group, and $R_2$ is (a) a straight or branched $C_6$–$C_{12}$ alkyl group, or (b) —OR'''' in which R'''' is a straight chain or branched $C_5$–$C_9$ alkyl group which may be substituted at the terminal carbon atom by a phenyl group.

4. The method of claim 3 wherein said compound is administered in a manner to protect against N-methyl-D-aspartate (NMDA) receptor mediated neurotoxicity.

5. A method according to claim 1 or claim 3 in which said pharmaceutical composition includes a carrier or diluent of an aqueous cosolvent solution comprising a pharmaceutically acceptable cosolvent, a micellar solution prepared with a surfactant, or combinations thereof.

6. The method of claim 5 which comprises selecting the carrier to be a solution of ethanol, a surfactant, and water.

7. The method of claim 5 which comprises selecting the carrier to be an emulsion comprising a triglycerides, lecithin, glycerol, an emulsifier, an antioxidant, and water.

8. A method according to claim 1 or claim 3 wherein the daily dosage of said compound is between 0.1 and 25 mg/kg.

* * * * *

UNITED STATES PATENT AND TRADEMARK OFFICE
CERTIFICATE OF CORRECTION

PATENT NO. : 5,521,215

DATED : May 28, 1996

INVENTOR(S) : Raphael Mechoulam, Mordechai Sokolovsky, Yoel Kloog and Anat Biegon It is certified that error appears in the above-indentified patent and that said Letters Patent is hereby corrected as shown below:

On the title page, item [75] Inventors;

Please change names to read in the order as follows:

Yoel Kloog, Mordechai Sokolovsky, Raphael Mechoulam and Anat Biegon

Signed and Sealed this

Third Day of September, 1996

Attest:

BRUCE LEHMAN

Attesting Officer

Commissioner of Patents and Trademarks